(12) United States Patent  (10) Patent No.: US 8,696,707 B2
Sutterlin, III  (45) Date of Patent: Apr. 15, 2014

(54) FACET JOINT STABILIZATION

(75) Inventor: Chester Sutterlin, III, Gainesville, FL (US)

(73) Assignee: Zyga Technology, Inc., Minneapolis, MN (US)

(*) Notice: Subject to any disclaimer, the term of this patent is extended or adjusted under 35 U.S.C. 154(b) by 2115 days.

(21) Appl. No.: 11/370,720

(22) Filed: Mar. 7, 2006

(65) Prior Publication Data
US 2006/0235391 A1  Oct. 19, 2006

Related U.S. Application Data

(60) Provisional application No. 60/659,629, filed on Mar. 8, 2005.

(51) Int. Cl.
A61B 17/70 (2006.01)
A61F 2/08 (2006.01)

(52) U.S. Cl.
USPC .................. 606/247; 623/13.13; 623/13.14

(58) Field of Classification Search
USPC ............. 606/252, 313, 247; 623/13.13, 13.14
See application file for complete search history.

(56) References Cited

U.S. PATENT DOCUMENTS

| 2,677,369 A | 5/1954 | Knowles |
| 3,426,364 A | 2/1969 | Lumb |
| 3,879,767 A | 4/1975 | Stubstad |
| 4,034,746 A | 7/1977 | Williams |
| 4,052,753 A | 10/1977 | Dedo |
| 4,349,921 A | 9/1982 | Kuntz |
| 4,502,161 A | 3/1985 | Wall |
| 4,553,273 A | 11/1985 | Wu |
| 4,554,914 A | 11/1985 | Kapp |
| 4,599,086 A | 7/1986 | Doty |
| 4,636,217 A | 1/1987 | Ogilvie |
| 4,743,256 A | 5/1988 | Brantigan |
| 4,790,303 A * | 12/1988 | Steffee .................... 606/300 |

(Continued)

FOREIGN PATENT DOCUMENTS

DE  9304368    5/1995
DE  20112123   9/2001

(Continued)

OTHER PUBLICATIONS

European Search Report; mailed Nov. 19, 2010.

(Continued)

Primary Examiner — Christian Sevilla
(74) Attorney, Agent, or Firm — Dicke, Billig & Czaja, PLLC

(57) ABSTRACT

Various implementations for therapy to facet joints connecting vertebrae are disclosed including: A) Facet joint stabilization that may be implemented using stabilization band that maintains tension between two anchors. The stabilization band may be retained in any one of a number of ways including the use of an anti-slip device such as a mechanically deformed crimp that abuts one of the anchors. B) Facet joint augmentation may be implemented by dilating the facet joint and inserting a facet joint spacer before adding a facet joint stabilization assembly. The facet joint augmentation may include connecting a tail section of the facet joint spacer to the first anchor used in the facet joint stabilization assembly. C) Facet joint immobilization may be implemented by inserting a fastener across the facet joint and into the vertebra so that the assembled fastener expands inside the vertebra.

4 Claims, 17 Drawing Sheets

(56) References Cited

U.S. PATENT DOCUMENTS

| | | |
|---|---|---|
| 4,834,757 A | 5/1989 | Brantigan |
| 4,877,020 A | 10/1989 | Vich |
| 5,092,866 A | 3/1992 | Breard |
| 5,147,404 A | 9/1992 | Downey |
| 5,156,616 A * | 10/1992 | Meadows et al. ............ 606/232 |
| 5,166,616 A | 11/1992 | Doddrell et al. |
| 5,415,659 A | 5/1995 | Lee |
| 5,415,661 A | 5/1995 | Holmes |
| 5,496,318 A | 3/1996 | Howland |
| 5,507,823 A | 4/1996 | Walston |
| 5,527,312 A | 6/1996 | Ray |
| 5,571,191 A | 11/1996 | Fitz |
| 5,609,634 A * | 3/1997 | Voydeville ................. 623/13.11 |
| 5,665,122 A | 9/1997 | Kambin |
| 5,681,310 A * | 10/1997 | Yuan et al. .................... 606/281 |
| 5,683,464 A | 11/1997 | Wagner |
| 5,697,889 A | 12/1997 | Slotman |
| 5,968,098 A | 10/1999 | Winslow |
| 6,019,792 A | 2/2000 | Cauthen |
| RE36,758 E | 6/2000 | Fitz |
| 6,102,948 A | 8/2000 | Brosnahan |
| 6,126,688 A | 10/2000 | McDonnell |
| 6,132,464 A | 10/2000 | Martin |
| 6,132,468 A | 10/2000 | Mansmann |
| 6,156,067 A | 12/2000 | Bryan |
| 6,179,874 B1 | 1/2001 | Cauthen |
| 6,280,442 B1 * | 8/2001 | Barker et al. .................... 606/60 |
| 6,287,313 B1 | 9/2001 | Sasso |
| 6,290,724 B1 | 9/2001 | Marino |
| 6,368,350 B1 | 4/2002 | Erickson |
| 6,440,168 B1 | 8/2002 | Cauthen |
| 6,443,988 B2 | 9/2002 | Felt |
| 6,458,159 B1 | 10/2002 | Thalgott |
| 6,485,518 B1 | 11/2002 | Cornwall |
| 6,540,747 B1 | 4/2003 | Marino |
| 6,544,265 B2 | 4/2003 | Lieberman |
| 6,562,046 B2 | 5/2003 | Sasso |
| 6,610,093 B1 | 8/2003 | Pisharodi |
| 6,652,585 B2 * | 11/2003 | Lange ........................ 623/17.11 |
| 6,652,587 B2 | 11/2003 | Felt |
| 6,679,915 B1 | 1/2004 | Cauthen |
| 6,733,531 B1 * | 5/2004 | Trieu ........................ 623/17.11 |
| 6,846,328 B2 | 1/2005 | Cauthen |
| 6,893,463 B2 | 5/2005 | Fell |
| 6,932,842 B1 | 8/2005 | Litschko |
| 6,966,930 B2 | 11/2005 | Arnin |
| 6,974,478 B2 | 12/2005 | Reiley |
| 6,986,771 B2 * | 1/2006 | Paul et al. .................... 606/254 |
| 6,989,011 B2 | 1/2006 | Paul |
| 7,001,431 B2 | 2/2006 | Bao |
| 7,041,136 B2 | 5/2006 | Goble |
| 7,087,084 B2 | 8/2006 | Reiley |
| 7,101,398 B2 | 9/2006 | Dooris |
| 7,115,131 B2 | 10/2006 | Engh |
| 7,115,132 B2 | 10/2006 | Errico |
| 7,115,142 B2 * | 10/2006 | Muhanna et al. .......... 623/13.11 |
| 7,147,665 B1 | 12/2006 | Bryan |
| 7,189,240 B1 | 3/2007 | Dekel |
| 7,270,681 B2 | 9/2007 | Cauthen |
| 7,270,687 B2 | 9/2007 | Doherty et al. |
| 7,291,169 B2 | 11/2007 | Hodorek |
| 7,371,238 B2 | 5/2008 | Soboleski |
| 7,377,942 B2 | 5/2008 | Berry |
| 7,468,075 B2 | 12/2008 | Lang |
| 7,476,252 B2 | 1/2009 | Foley |
| 7,591,851 B2 | 9/2009 | Winslow |
| 7,618,451 B2 | 11/2009 | Berez |
| 7,708,761 B2 | 5/2010 | Petersen |
| 7,744,612 B2 | 6/2010 | Blain |
| 7,776,090 B2 | 8/2010 | Winslow |
| 7,846,183 B2 | 12/2010 | Blain |
| 7,922,766 B2 | 4/2011 | Grob |
| 7,927,374 B2 | 4/2011 | Duggal |
| 7,935,134 B2 | 5/2011 | Reglos |
| 7,938,836 B2 | 5/2011 | Ainsworth |
| 7,938,857 B2 | 5/2011 | Garcia |
| 7,955,355 B2 | 6/2011 | Chin |
| 7,998,172 B2 | 8/2011 | Blain |
| 8,100,955 B2 | 1/2012 | Blain |
| 8,343,189 B2 | 1/2013 | Assell et al. |
| 2001/0051807 A1 * | 12/2001 | Grafton .......................... 606/72 |
| 2002/0026244 A1 | 2/2002 | Trieu |
| 2002/0055737 A1 | 5/2002 | Lieberman |
| 2002/0120270 A1 * | 8/2002 | Trieu et al. ..................... 606/61 |
| 2002/0143329 A1 * | 10/2002 | Serhan et al. ................... 606/61 |
| 2002/0151895 A1 | 10/2002 | Soboleski |
| 2003/0028250 A1 | 2/2003 | Reiley |
| 2003/0176871 A1 | 9/2003 | Pavlov |
| 2003/0208202 A1 | 11/2003 | Falahee |
| 2003/0220643 A1 * | 11/2003 | Ferree ............................. 606/61 |
| 2004/0010312 A1 | 1/2004 | Enayati |
| 2004/0049280 A1 | 3/2004 | Cauthen |
| 2004/0087954 A1 | 5/2004 | Allen |
| 2004/0143332 A1 | 7/2004 | Krueger |
| 2004/0143333 A1 | 7/2004 | Bain et al. |
| 2004/0153159 A1 | 8/2004 | Cauthen |
| 2004/0225360 A1 | 11/2004 | Malone |
| 2004/0236328 A1 * | 11/2004 | Paul et al. ....................... 606/61 |
| 2004/0260287 A1 | 12/2004 | Ferree ............................. 606/61 |
| 2005/0021029 A1 * | 1/2005 | Trieu et al. ..................... 606/61 |
| 2005/0027361 A1 | 2/2005 | Reiley |
| 2005/0049705 A1 | 3/2005 | Hale |
| 2005/0076974 A1 | 4/2005 | Honkura et al. |
| 2005/0080486 A1 | 4/2005 | Fallin |
| 2005/0085912 A1 | 4/2005 | Arnin |
| 2005/0119748 A1 | 6/2005 | Reiley |
| 2005/0125062 A1 * | 6/2005 | Biedermann et al. ...... 623/17.11 |
| 2005/0143818 A1 | 6/2005 | Yuan |
| 2005/0143825 A1 | 6/2005 | Enayati |
| 2005/0159746 A1 | 7/2005 | Grob |
| 2005/0177240 A1 | 8/2005 | Blain |
| 2005/0197700 A1 | 9/2005 | Boehm |
| 2005/0197706 A1 | 9/2005 | Hovorka |
| 2005/0251256 A1 | 11/2005 | Reiley |
| 2005/0273100 A1 * | 12/2005 | Taylor ............................. 606/61 |
| 2006/0009847 A1 | 1/2006 | Reiley |
| 2006/0036243 A1 | 2/2006 | Sasso |
| 2006/0036323 A1 | 2/2006 | Carl |
| 2006/0041311 A1 | 2/2006 | McLeer |
| 2006/0064099 A1 | 3/2006 | Pavlov |
| 2006/0084977 A1 | 4/2006 | Lieberman |
| 2006/0085068 A1 | 4/2006 | Barry |
| 2006/0089633 A1 | 4/2006 | Bleich et al. |
| 2006/0111779 A1 | 5/2006 | Petersen |
| 2006/0111780 A1 | 5/2006 | Petersen |
| 2006/0111781 A1 | 5/2006 | Petersen |
| 2006/0111782 A1 | 5/2006 | Petersen |
| 2006/0116768 A1 | 6/2006 | Krueger |
| 2006/0122701 A1 | 6/2006 | Kiester |
| 2006/0149374 A1 * | 7/2006 | Winslow et al. ........... 623/17.11 |
| 2006/0155297 A1 | 7/2006 | Ainsworth |
| 2006/0190081 A1 | 8/2006 | Kraus |
| 2006/0217754 A1 | 9/2006 | Boehm, Jr. et al. |
| 2006/0235391 A1 | 10/2006 | Sutterlin |
| 2006/0235403 A1 | 10/2006 | Blain |
| 2006/0235409 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2006/0241648 A1 | 10/2006 | Bleich et al. |
| 2006/0241758 A1 | 10/2006 | Peterman |
| 2006/0247632 A1 | 11/2006 | Winslow |
| 2006/0247633 A1 | 11/2006 | Winslow |
| 2006/0276790 A1 | 12/2006 | Dawson |
| 2006/0276907 A1 | 12/2006 | Boyer |
| 2007/0032790 A1 | 2/2007 | Aschmann |
| 2007/0055236 A1 | 3/2007 | Hudgins |
| 2007/0055252 A1 | 3/2007 | Blain |
| 2007/0055373 A1 | 3/2007 | Hudgins |
| 2007/0067032 A1 | 3/2007 | Felt et al. |
| 2007/0083265 A1 | 4/2007 | Malone |
| 2007/0083266 A1 | 4/2007 | Lang |
| 2007/0088358 A1 | 4/2007 | Yuan |
| 2007/0100450 A1 | 5/2007 | Hodorek |

(56) References Cited

U.S. PATENT DOCUMENTS

| | | |
|---|---|---|
| 2007/0118218 A1 | 5/2007 | Hooper |
| 2007/0123863 A1 | 5/2007 | Winslow |
| 2007/0135814 A1 | 6/2007 | Farris |
| 2007/0135919 A1 | 6/2007 | Aebi |
| 2007/0149976 A1 | 6/2007 | Hale |
| 2007/0161991 A1 | 7/2007 | Altarac |
| 2007/0167946 A1 | 7/2007 | Triplett et al. |
| 2007/0179608 A1 | 8/2007 | Ek |
| 2007/0225813 A1 | 9/2007 | Haines |
| 2007/0276370 A1 | 11/2007 | Altarac |
| 2007/0276498 A1 | 11/2007 | Aebi |
| 2007/0276499 A1 | 11/2007 | Paul |
| 2008/0009875 A1 | 1/2008 | Sankaran |
| 2008/0027543 A1 | 1/2008 | Eisermann |
| 2008/0027547 A1 | 1/2008 | Yu |
| 2008/0033440 A1 | 2/2008 | Moskowitz |
| 2008/0045954 A1 | 2/2008 | Reiley |
| 2008/0051901 A1 | 2/2008 | De Villiers |
| 2008/0091199 A1 | 4/2008 | Cragg |
| 2008/0097613 A1 | 4/2008 | Reiley |
| 2008/0119933 A1 | 5/2008 | Aebi |
| 2008/0125814 A1 | 5/2008 | Yuan |
| 2008/0132951 A1 | 6/2008 | Reiley |
| 2008/0140121 A1 | 6/2008 | McLeer |
| 2008/0143818 A1 | 6/2008 | Ferren |
| 2008/0154305 A1 | 6/2008 | Foley |
| 2008/0208249 A1 | 8/2008 | Blain |
| 2008/0262555 A1 | 10/2008 | Assell |
| 2009/0062920 A1 | 3/2009 | Tauber |
| 2009/0088846 A1 | 4/2009 | Myung |
| 2009/0138053 A1 | 5/2009 | Assell |
| 2009/0177205 A1 | 7/2009 | McCormack |
| 2009/0234458 A1 | 9/2009 | De Villiers |
| 2009/0264928 A1 | 10/2009 | Blain |
| 2010/0131008 A1 | 5/2010 | Overes |
| 2010/0228288 A1 | 9/2010 | Blain |
| 2010/0249937 A1 | 9/2010 | Blain |
| 2010/0274286 A1 | 10/2010 | Blain |
| 2010/0286778 A1 | 11/2010 | Eisermann |
| 2010/0292797 A1 | 11/2010 | Lindner |
| 2011/0022089 A1 | 1/2011 | Assell |
| 2011/0040301 A1 | 2/2011 | Blain |
| 2011/0060366 A1 | 3/2011 | Heim |
| 2011/0082503 A1 | 4/2011 | Blain |
| 2011/0307061 A1 | 12/2011 | Assell et al. |
| 2011/0313456 A1 | 12/2011 | Blain |

FOREIGN PATENT DOCUMENTS

| | | |
|---|---|---|
| DE | 202009006906 | 7/2009 |
| EP | 381588 | 8/1990 |
| FR | 2681525 | 3/1993 |
| FR | 2717675 | 9/1995 |
| WO | 9310725 | 6/1993 |
| WO | 9405235 | 3/1994 |
| WO | 0234147 | 2/2002 |
| WO | 02/45765 A2 | 6/2002 |
| WO | 02065954 | 8/2002 |
| WO | 2005072661 | 8/2005 |
| WO | 2005076974 | 8/2005 |
| WO | 2006/020464 A2 | 2/2006 |
| WO | 2006065774 | 6/2006 |
| WO | 2006096803 | 9/2006 |
| WO | 2007019215 | 2/2007 |
| WO | 2009143496 | 11/2009 |
| WO | 2011011621 | 1/2011 |

OTHER PUBLICATIONS

"Dynesys® Dynamic Stabiliation System: A Guide for Patients", 5 pgs, as listed on http://www.zimmer.com/ctl?template=IN&action=1&op=global&id=9163&pr=Y on Mar. 8, 2007, however, the document lists the most recent update as Jul. 21, 2005.

"Dynesys® Dynamic Stabilitation System", 4 pgs, as listed on http://www.zimmer.com/ctl?template=IN&action=1&op=global&id=9165&pr=Y on Mar. 8, 2007, however, the document lists the most recent update as Jul. 21, 2005.

\* cited by examiner

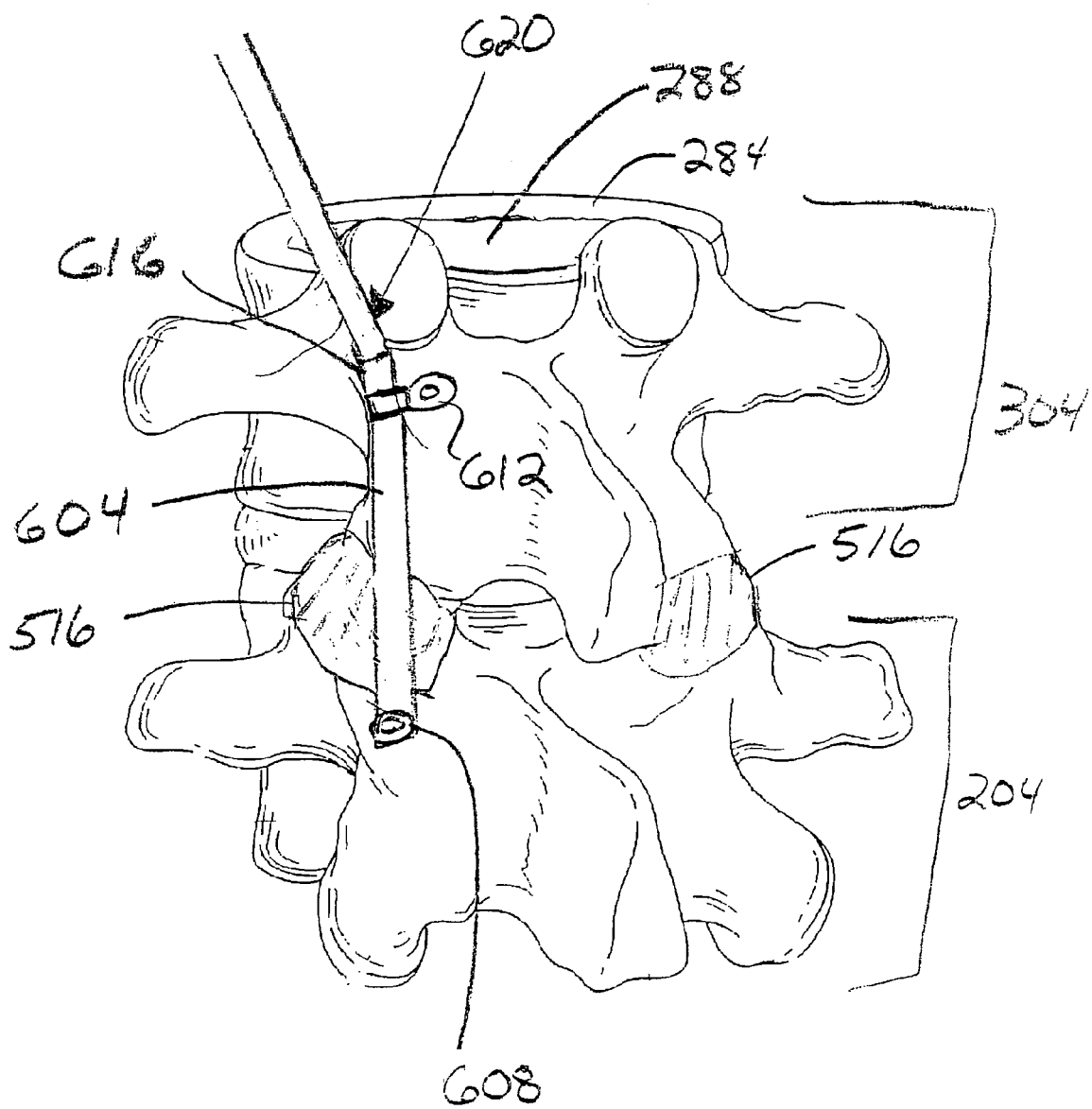

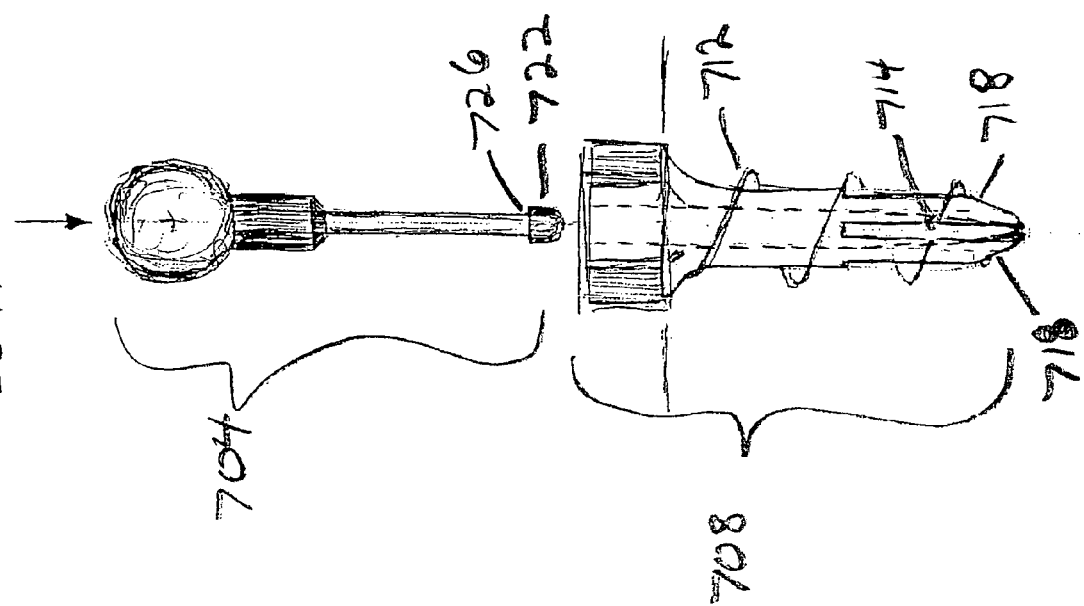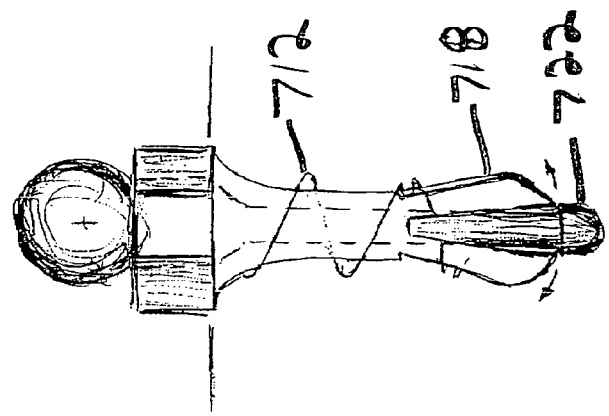

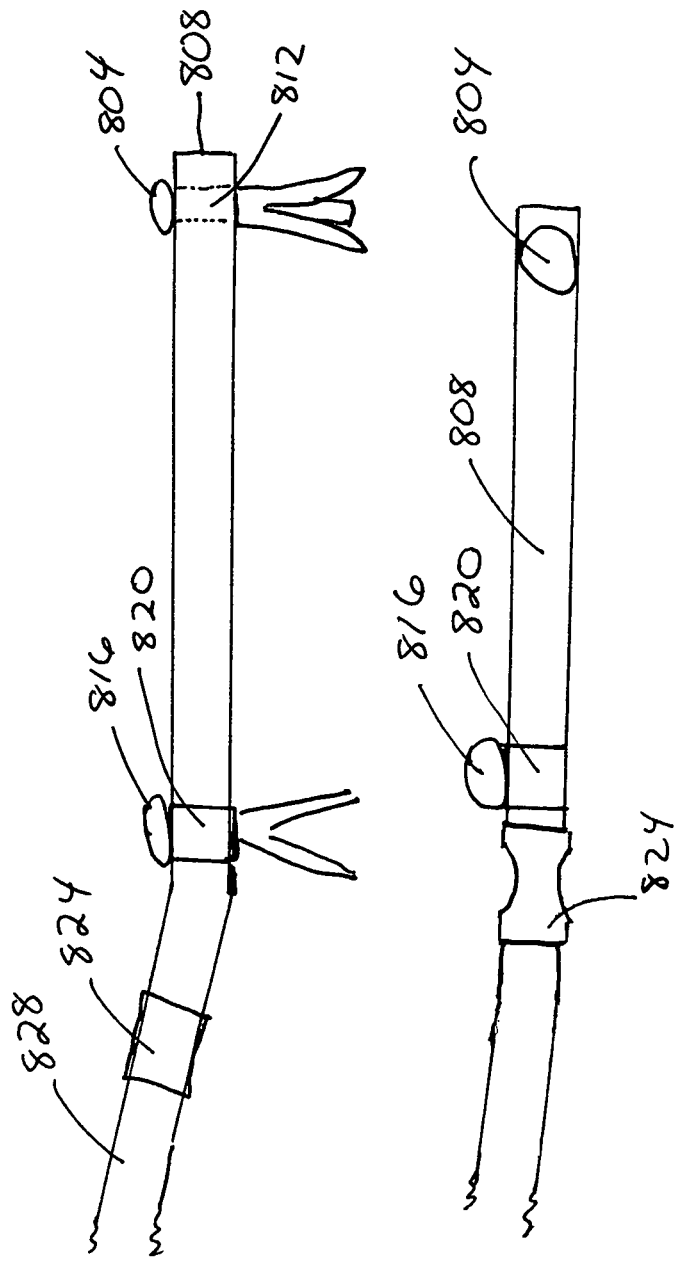

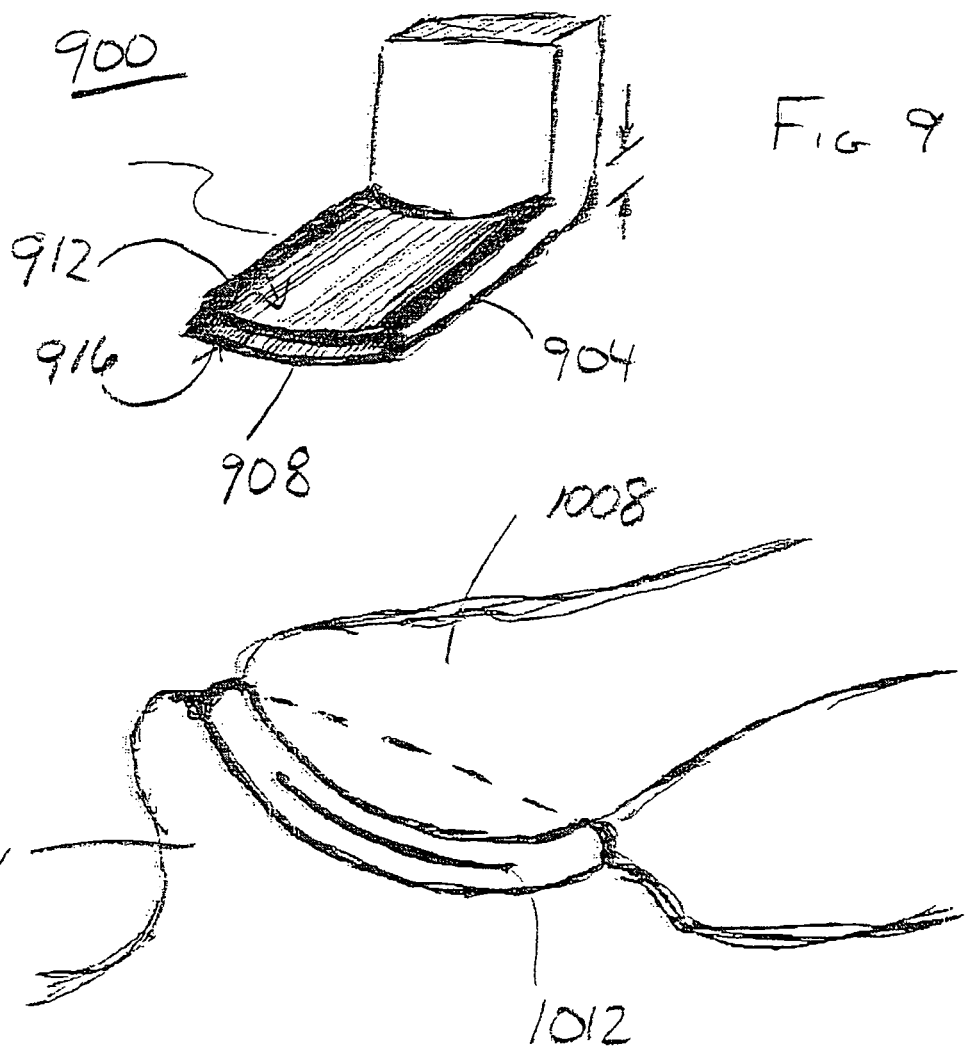

FACET JOINT STABILIZATION

This application claims priority to and incorporates by reference herein, U.S. Provisional Patent Application No. 60/659,629 filed Mar. 8, 2005.

BACKGROUND OF THE INVENTION

1. Field of the Invention

The present invention relates generally to spinal devices introduced percutaneously through tissue to an access point on the spine in a minimally invasive, low trauma manner, to provide therapy to the spine. The devices may be deployed in situ to supplement physiologic structures of the spine through instrumentation cannula that are generally introduced via a posterior approach into a surgically prepared space. The spinal devices may be used to augment and stabilize one or more facet joints on the posterior of the spinal column.

The spinal column is a complex system of bone segments (vertebral bodies and other bone segments) that are in most cases separated from one another by discs in the intervertebral spaces (sacral and coccygeal vertebrae are an exception). FIG. 1 shows the various segments of a human spinal column as viewed from the side. In the context of the present invention, a "motion segment" is composed of adjacent vertebrae, i.e., an inferior and a superior vertebra, and the intervertebral disc space separating the two vertebrae, whether denucleated space or with intact or damaged spinal discs. Each motion segment contributes to the overall flexibility of the spine and contributes to the overall ability of the spine to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. While often called a column, individual vertebrae are not aligned so that they form a traditional column. Instead, the spine is composed of a number of curved segments. When vertebrae degrade, the degraded vertebrae may alter the desirable curvature of the spine in undesirable ways.

The individual vertebral bodies within the sections are identified by number starting at the vertebral body closest to the head. Of particular interest in this application are the vertebral bodies in the lumbar section and the sacral section as a large concentration of back pain is attributed to problems between the bottom two vertebrae in the lumbar section or between the bottom lumbar vertebra and the sacrum. As the various vertebral bodies in the sacral section are usually fused together in adults, it is sufficient and perhaps more descriptive to merely refer to the sacrum rather than the individual sacral components.

It is useful to set forth some of the standard medical vocabulary before getting into a more detailed discussion of the background of the present invention. In the context of the this discussion: anterior refers to in front of the spinal column (ventral), and posterior refers to behind the column (dorsal); cephalad means towards the patient's head (sometimes "superior"); caudal (sometimes "inferior") refers to the direction or location that is closer to the feet.

The individual motion segments within the spinal columns allow movement within constrained limits and provide protection for the spinal cord. The discs are important to bear and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the height between adjacent vertebral bodies is reduced and this causes additional problems including pain.

Many solutions have been proposed to address defects in the shape or operation of discs between vertebral bodies in the spine. However, the stack of discs and vertebral bodies on the anterior side of the spine is not the entirety of the spine. The present disclosure addresses treatments for joints to the posterior of the spinal column.

Vertebrae differ from person to person and from top to bottom of the spinal column within a particular person. Thus, the size, shape, and angular projections of the protrusions (called processes) from the vertebrae vary considerably from these examples that are typical of the lumbar section of the spine. These views discussed below while not perfect representations of every vertebrae, are sufficient to introduce the various components of interest.

While it is useful to see two adjacent vertebrae in their anatomic relationship to one another, it may be more useful to start with a view of a single vertebra.

FIG. 2 is a top perspective view of a single vertebra 204. The vertebra has a hard outer shell of cortical bone 284 and an interior of cancellous bone 288.

The spinal cord (not shown) is protected in the spinal foramen 292 formed by the two pedicles 212, 216 and the two laminae 220, 224. Extending from the pedicles are two transverse processes 228, 232. Extending from the midline of the vertebra where the two laminae meet is the spinous process 236. These three processes serve as connection points for ligaments and muscle.

Vertebrae move relative to one other in order to allow the spine to bend forward (flexion), bend backward (extension), bend to the right or left (lateral bending), twist (rotate in the z-axis) and other forms of movement. While the disc 280 plays an important part in this movement in absorbing shocks and distributing loads, there are also joints on the posterior side of the spinal column that allow for movement of a vertebra relative to an adjacent vertebra.

These joints are called facet joints. Most vertebrae have four facet joints. Two facet joints between a particular vertebra and the adjacent cephalad vertebra and two facet joints between the particular vertebra and the adjacent caudal vertebra.

The components of the facet joints are the superior articular process 240 and 244 and the inferior articular process 248 and 252.

FIG. 3 is a rear perspective view of a motion segment 200 with a lower (more caudal) vertebra 204 and a higher (more cephalad) vertebra 304. The anterior portion of the vertebra is the vertebral body 208, 308. Between the two vertebral bodies 208 308 is a disc 280. The spinous processes 236 and 336 and the transverse processes 228, 232, 328, 332 are visible in this view.

The facet joint portion of the superior articular processes 240 and 244 for vertebra 204 are engaged by the inferior articular processes 348 and 352 of vertebra 304. The superior articular processes 340, 344 for the vertebra 308 are visible as they would engage with the inferior articular processes from the next more cephalad vertebra. Likewise the inferior articular processes 248, 252 of vertebra 204 would engage with the superior articular processes of the next more caudal vertebra. A neuralforamen 356 (sometimes neural foramen) is partially visible in FIG. 3. There is another neuralforamen on the opposite side. The neuraloforamina provide a passage for the nerves connecting to the spinal cord. If this passage way is constricted, the constriction called stenosis of the neuralforamina can cause pain or other neural symptoms.

FIG. 4 is a posterior view of the sacral 116, and coccygeal 120 sections of a spine. During development, the five individual vertebrae fuse together to form a sacrum 404 and four vertebrae fuse together to form the coccyx 408. While fused together, the initially distinct vertebrae of the sacrum are sometimes referenced. The S1 vertebra is the top vertebra in the sacrum 404 and is adjacent to the L5 vertebra that is the most caudal of the five lumbar section vertebrae. The inferior articular processes of the L5 vertebra engage with the articular processes 412 and 416 of the sacrum 404. These processes are effectively the superior articular processes of the S1 vertebra.

FIG. 5 is an enlarged cross section of a facet joint 500 between a superior articular process 504 and an inferior articular process 508 of an adjacent more cephalad vertebra. The facet joints are synovial joints; each facet joint having two opposing bony surfaces 504 and 508 with cartilage 512 between them and a joint capsule 516 around the facet. More specifically, synovial fluid 520 is contained inside the facet joint 500 by the joint capsule 516, a watertight sac of soft tissue and ligaments that fully surrounds and encloses the facet joint, which keeps the joint surfaces lubricated. The ends of the superior articular process 504 and the inferior articular process 508 make up the synovial facet joint 500 are normally covered with articular, hyaline cartilage 512 that allows the bones to glide against one another providing the flexibility that allows the movement of vertebrae relative to one another.

While others have advocated prosthetic replacement of damaged facet joints, in practice it is difficult to implement a prosthetic facet joint for a variety of reasons including the variability in facet joint geometry from facet joint to facet joint, and the high level of interaction between the facet joint and the other components in the spinal column. Another therapeutic treatment of the facet joint is to affix the superior articular process to the inferior articular process using a facet screw. While this radical therapy may alleviate symptoms associated with a degenerated facet joint, it also sacrifices some of the ability of the motion segment to move and thus sacrifices some of the ability of the spinal column to move in a natural manner.

Facet joints that are out of the preferred anatomic position may lead to vertebrae that are out of preferred alignment with one another. This mal-aligned vertebrae may impinge in the spaces for the spinal cord and the nerves running outward from the spinal cord. The reduction in space called stenosis may cause pain, numbness, or other problems.

Thus, there is an unmet need for additional therapies applicable to facet joints to stabilize and perhaps augment the facet joint to alleviate problems without initial resort to the more radical therapies of replacing the facet joint with a prosthetic joint or fixation of the facet joint and the inherent loss of natural movement of that motion segment. The use of the less radical treatment options disclosed below may be followed by a more radical treatment option at a later date should the need for treatment evolve to require the more radical treatment.

SUMMARY OF THE DISCLOSURE

The many variations of treatment in this disclosure may be summarized as belonging to three classes of treatment for facet joints.

Facet joint stabilization may be implemented using stabilization band that maintains tension between two anchors. The stabilization band may be retained in any one of a number of ways including the use of an anti-slip device such as a mechanically deformed crimp that abuts one of the anchors.

Facet joint augmentation may be implemented by dilating to impose distraction between components of the facet joint and inserting a facet joint spacer before adding a facet joint stabilization assembly. The facet joint augmentation may include connecting a tail section of the facet joint spacer to the first anchor used in the facet joint stabilization assembly.

Facet joint immobilization may be implemented by inserting a fastener across the facet joint and into the vertebra so that the assembled fastener expands inside the vertebra. The facet joint immobilization may be implemented by installing the fastener through both a stabilization band and the facet joint being immobilized.

In addition to the various classes of therapy, various tools and methods that are useful in implementing the various disclosed therapies are disclosed.

Other systems, methods, features and advantages of the invention will be or will become apparent to one with skill in the art upon examination of the following figures and detailed description. It is intended that all such additional systems, methods, features, and advantages be included within this description, be within the scope of the invention, and protected by the accompanying claims.

BRIEF DESCRIPTION OF THE FIGURES

This invention may be better understood with references to the following figures. The components in the figures are not necessarily to scale, emphasis instead being placed upon illustrating the principles of the invention. Moreover, in the figures, like reference numerals designate corresponding parts throughout different views.

FIG. 6 is a rear perspective view of a motion segment with an implementation of a facet joint stabilization assembly.

FIG. 7A shows details of a cannulated slit screw adapted to be driven into an appropriate bore hole and expanded by the insertion of an expander pin.

FIG. 7B is a side view of an anchor after insertion of the expander pin.

FIG. 8A is a side view of an illustration of an implementation with a first anchor 804 engaged with a stabilization band 808 through a pre-formed opening 812.

FIG. 8B is a top view of the facet joint stabilization assembly in FIG. 8A.

FIG. 9 is a perspective view of the distal end of an implementation of a facet joint dilator 900.

FIG. 10 is a caudal entry view of a facet joint without the joint capsule.

DETAILED DESCRIPTION

Figure 1:
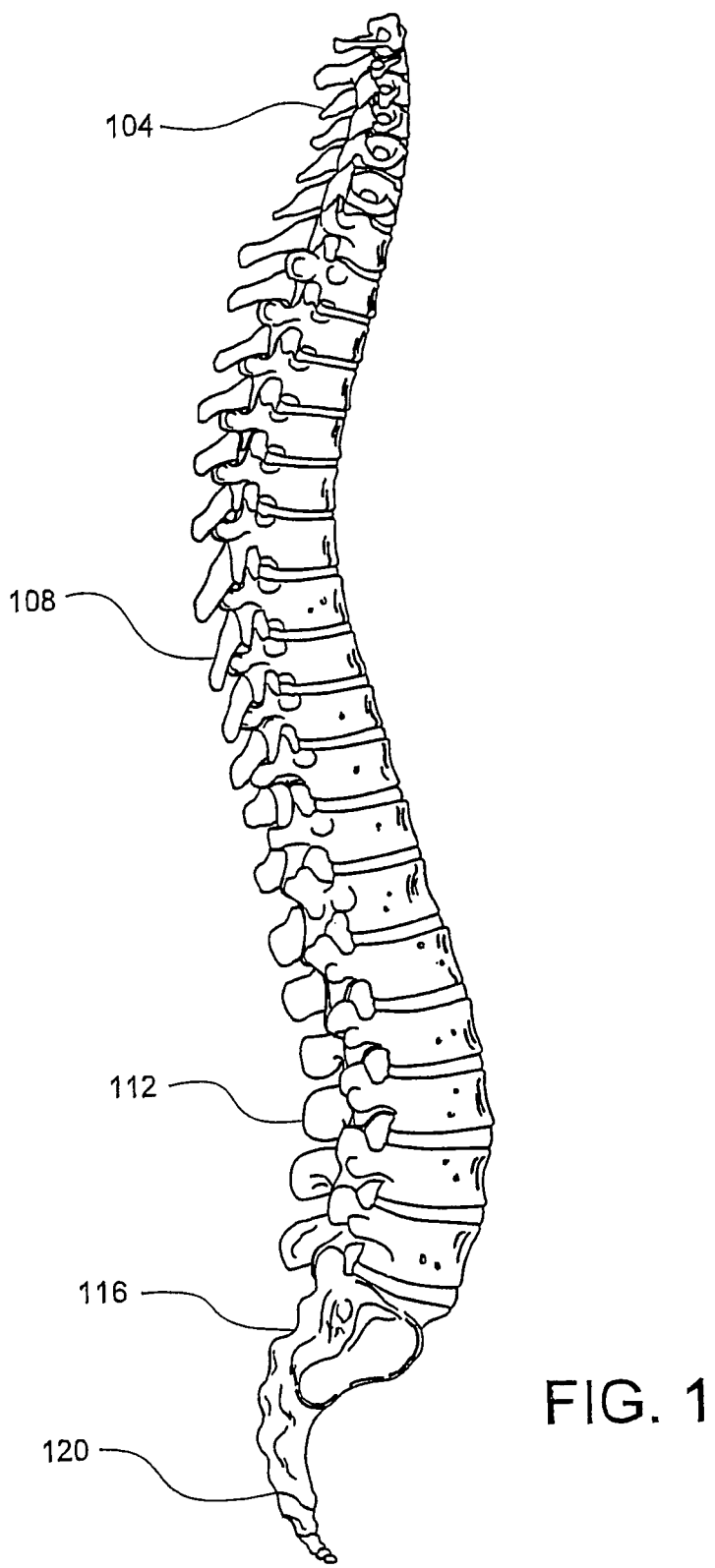
FIG. 1 is a side view of a human spine.
Figure 2:
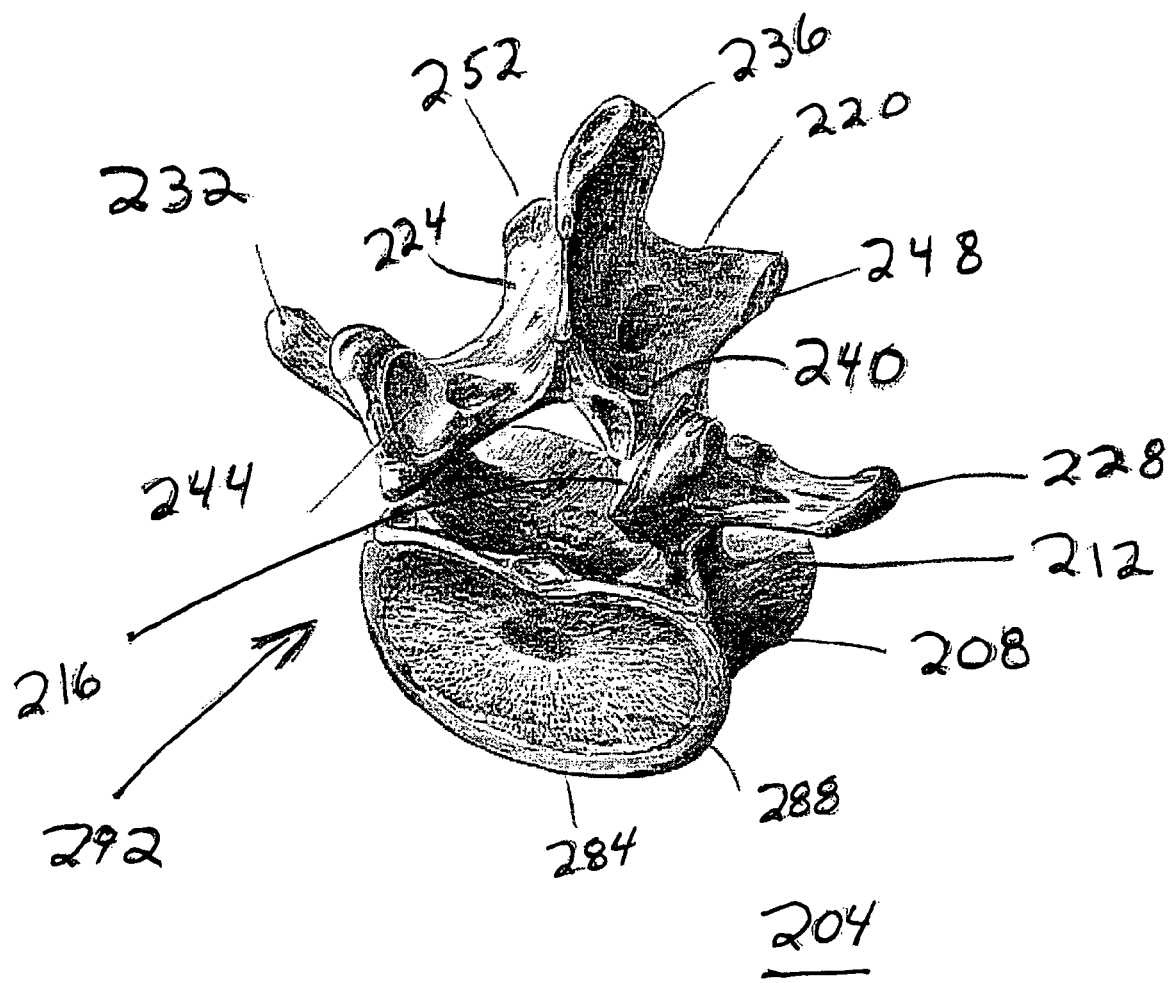
FIG. 2 is a top perspective view of a single vertebra.
Figure 3:
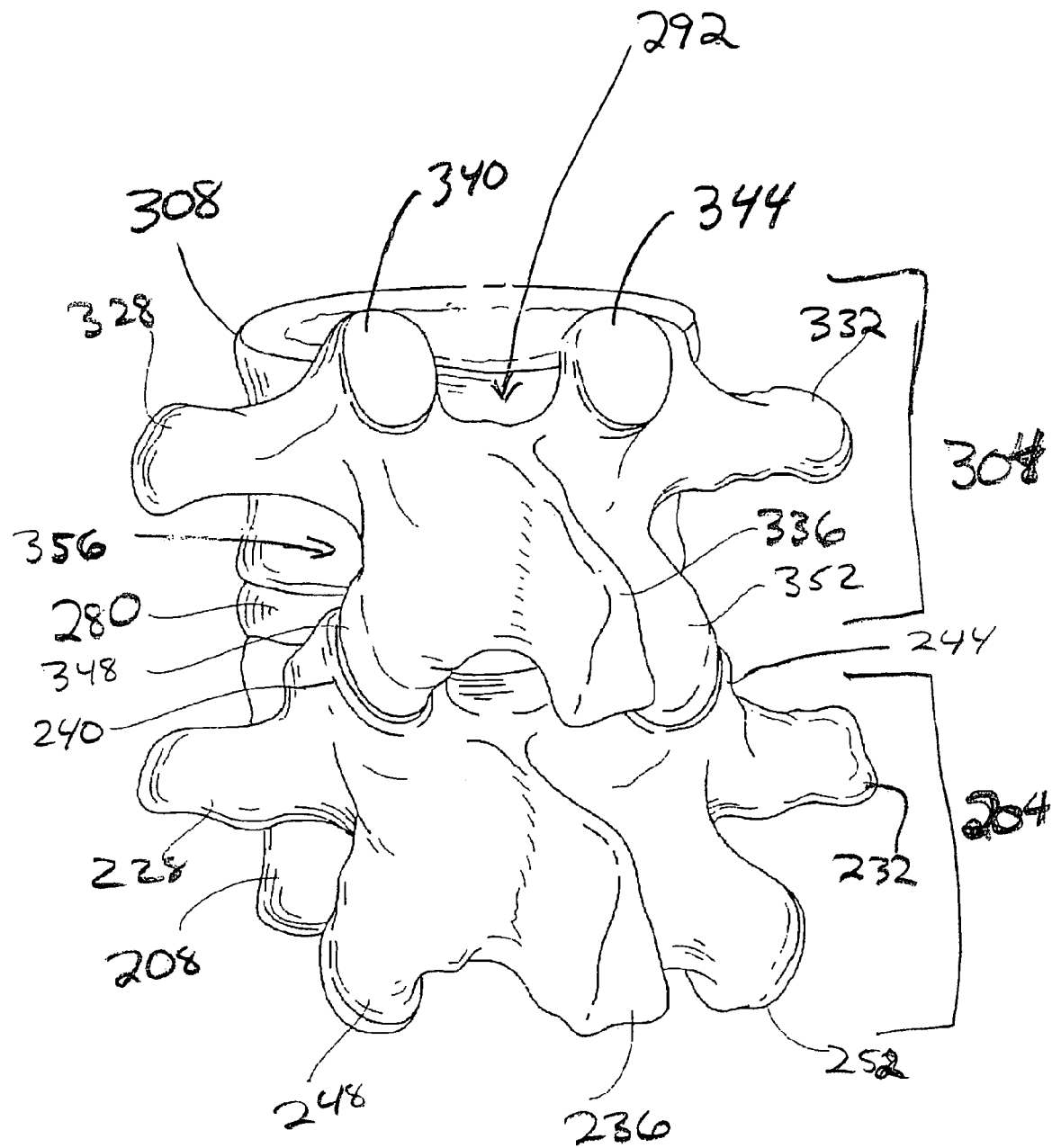
FIG. 3 is a rear perspective view of a motion segment 200 with a lower (more caudal) vertebra 204 and a higher (more cephalad) vertebra 304.

As described above, a motion segment will have two facet joints, one on each side. Most vertebrae will be involved with four facet joints, two joints with the adjacent more cephalad vertebra and two joints with the adjacent more caudal vertebra. While the therapies described below may be implemented bilaterally, the surgeon may find it appropriate to apply a particular therapy to one facet joint and not to the corresponding facet joint.

Facet Joint Stabilization Assembly.

FIG. 6 introduces a first form of therapy for a facet joint, a facet joint stabilization assembly 600. In the context of the present disclosure the term "assembly" refers to multiple components, which may or may not be contiguous, and that individual components may themselves be configured as sub-assemblies that in turn include a plurality of components.

A facet stabilization band 604 is anchored between a first anchor 608 and a second anchor 612. The first and second anchors may be a number of different types of anchors and the first anchor may operate based on a different concept than the second anchor. In FIG. 6, both anchors are engaged with vertebrae using fasteners that traverse the hard dense cortical bone 284 into the cancellous bone 288 beneath. As shown in FIG. 6, the facet stabilization band 604 may pass through a portion of the second anchor 612. As the stabilization band is pulled through the portion of the second anchor 612, a tensile force will be introduced on the portion of the stabilization band between the first anchor and the second anchor that will tend to pull the two anchors closer together if the spinal column will allow the movement. Thus, the selection of the points of placement of the two anchors allows the surgeon to promote movement of the inferior and superior articular processes of a facet joint relative to one another. By selecting the placement of the anchors and the tension on the stabilization band, the surgeon can effectively reposition the two components of the facet joint and thus influence the relative position of the two vertebrae that meet at the facet joint. This repositioning can impact the curvature of the spine and at least partially correct for curvature that deviates from the anatomically desirable curvature. Releasing the stabilization band 604 may remove the tensile force and the force that maintains the relative position of the two articular processes for that facet joint.

A retainer means 616 that engages the stabilization band 604 to prevent movement back through the second anchor 612 towards the first anchor 608 may be used to prevent the release of the stabilization band 604. After the stabilization band 604 is engaged with the retainer 616 the retainer is positioned so that the retainer cannot move such as by placing the retainer abutting the second anchor and sizing the retainer so that it cannot pass through thesecond anchor. After the stabilization band it retained relative to the second anchor, a portion of the stabilization band may be removed such as by cutting the stabilization band near the retainer as indicated by arrow 620.

While FIG. 6 helps illustrate concepts relevant to a facet joint stabilization assembly, FIG. 6 is by no means exhaustive of the many variations in how the facet joint stabilization assembly may be implemented.

The facet joint 500 receiving therapy in FIG. 6 is a facet joint between two lumbar vertebrae. While adjustments may need to be made for size and angles, a facet joint stabilization assembly may be applied between the L5 vertebra and the sacrum, or on a more cephalad motion segment involving the cervical or dorsal portions of the spine. (See 104 and 108 of FIG. 1). As mentioned above, the therapy may be applied bilaterally to a pair of facet joints between two vertebrae. Facet joint stabilization assemblies may be applied to more than one motion segment.

Figure 4:
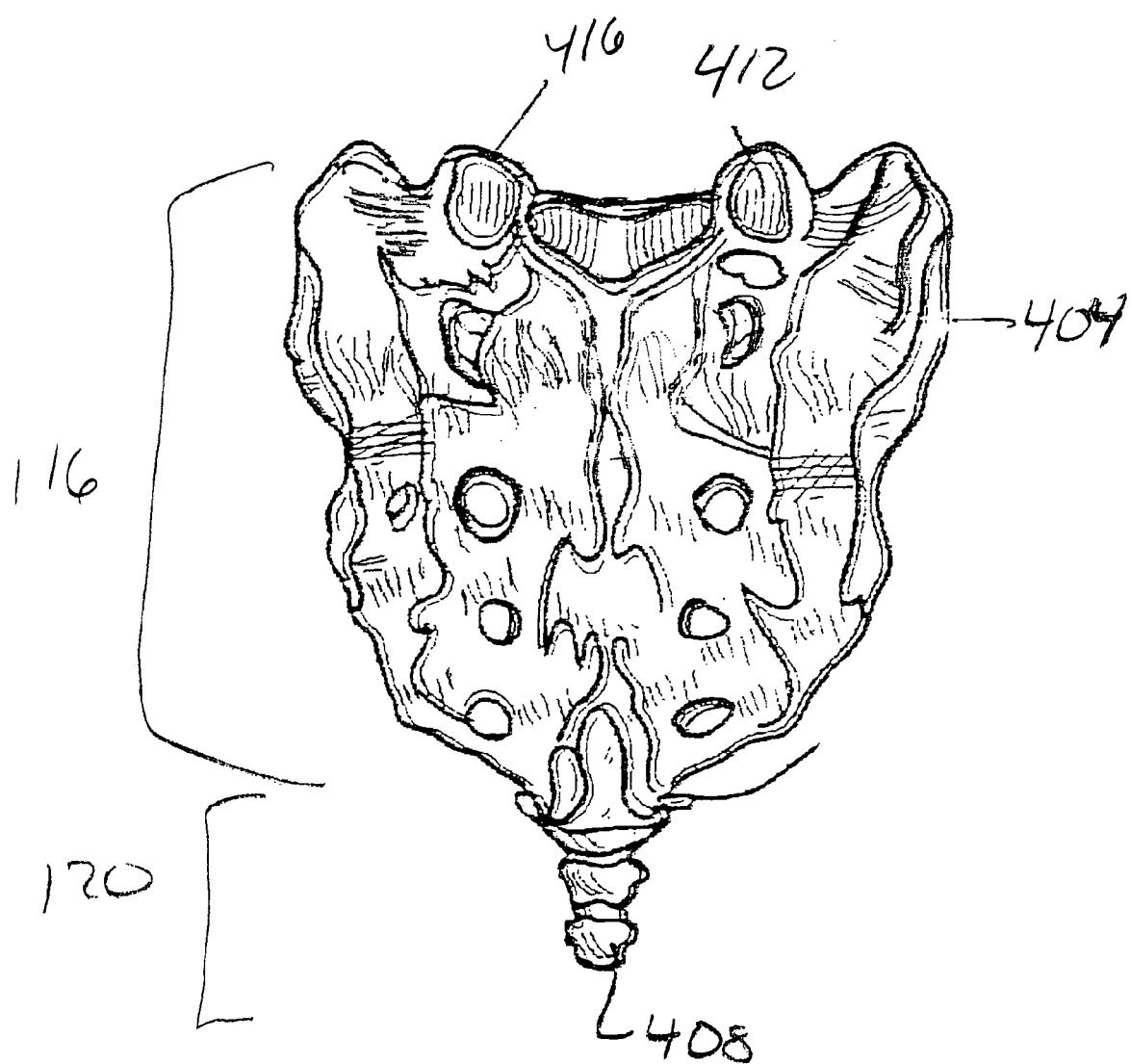
FIG. 4 is a posterior view of the sacral 116, and coccygeal 120 sections of a spine.

The first anchor is shown in FIG. 6 as anchored by a fastener into the same vertebra as the superior articular process. The first anchor may be placed into a more caudal vertebra including one of the components of the sacrum 404. If the facet joint receiving therapy is a facet joint between the L5 vertebra and the S1 vertebra of the sacrum, then the first anchor may be placed into the sacrum either close to the facet joint or further down the sacrum into something other than the S1 vertebra. As seen in FIG. 4, the sacrum has a number of foramina. The first anchor means may be a foraminal hook that is adapted to hook into one of the sacral foramen. The first anchor means may be a laminal hook that is adapted to engage the one of the laminae. Hooks are viable as anchors as the hook will be under tension after the stabilization band is pulled and retained.

The first anchor means may be a bone screw known in the art including a cortical bone screw, a cancellous bone screw, and a facet screw. The cortical bone 284 is difficult to screw into but the bone screw may use self-tapping threads. The anchor may engage a bore that is created in the vertebra such as through use of a drill or a punch.

The first anchor means may include any of the permanent surgical fasteners such as staples known in the art that are suitable to engage the first end of the stabilization band and cortical bone. Surgical fasteners that are intended to dissolve after a period of time are not likely to be selected by a surgeon for use in this application.

The anchor may engage the vertebra at a variety of locations depending on the desired placement of the anchors. The anchor may be placed in the pedicle. The depth of the anchor should be selected to ensure that the anchor does not impinge on any part of the spinal canal and thus damage or irritate the spinal cord or the nerves running from the spinal cord. The anchor may also engage: the spinous process; the laminae; pars interarticularis (between lamina and pedicle); articular processes, and other suitable structures.

The fasteners may be cannulated along the long axis so as to be adapted for delivery over a guide wire.

The fasteners used in anchors may use snap pins that engage a portion of the anchor that is adapted to receive and retain the snap pin. A first part of the anchor is engaged with the cortical bone perhaps through a previously created bore hole in the cortical bone. The snap pin engages the item to be anchored and is extended into the first part of the anchor where the snap pin is retained, thus anchoring the item to be anchored to the first part of the anchor which is in-turn anchored in the vertebra.

The fasteners used in anchors may be adapted to expand a portion of the anchor within the vertebra to increase the purchase of the anchor, thus making it less likely that the anchor will pull out. FIG. 7A shows details of a cannulated slit screw 708 adapted to be driven into an appropriate bore hole and expanded by the insertion of an expander pin 704 as shown in FIG. 7B.

The base 708 of the anchor is initially effectively a threaded rod. The external threads 712 (illustrated here conceptually as the actual thread choice is not limited to a particular type of bone threads) are sized to engage the outer surface of the bore in the bone. The thread may have discontinuities 714 between the base fingers 718. Introduction of the expander pin 704 splays the base fingers 718. The end cap 722 of the expander pin 704 extends beyond the splayed base fingers 718 and the base fingers 718 engage with a shoulder 722 so that the expander pin 704 is locked in place. Other implementations may use an expander tip that is threaded so that the upper portion of the expander tip engages with corresponding female threads in the interior of the anchor base. An implementation using threaded engagement between the anchor components would not need an end cap with a shoulder in order to lock the expander pin in place.

FIG. 6 shows the first anchor to be caudal to the facet joint receiving therapy. The first anchor may be cephalad to the facet joint with the second anchor being caudal. Thus, the first anchor may be connected to the vertebra 304 with the inferior articular process that is part of the facet joint receiving therapy. The first anchor may be connected to a more cephalad vertebra.

The second anchor may be connected in the same locations and manners as the first anchor. The only restriction on the placement of the second anchor is that it must work with the placement of the first anchor so that tension on the stabilization band provides the desired movement of the anchors towards each other.

The first anchor serves to anchor a first end of the stabilization band. In order to achieve that objective, the first anchor must engage with a portion of the spinal column and must engage with the first end of the stabilization band. There are a number of ways that the first anchor may engage with a first end of the stabilization band. One way is for a portion of the anchor means (such as a snap pin or a bone screw) to pass through a pre-formed hole in the first end of the stabilization band. In this implementation, the pre-formed hole may be created as part of the manufacturing process of the stabilization band or during preparations for insertion of the stabilization band before it is Introduced into the body. The pre-formed hole may be added to the stabilization band in situ but before the insertion of a portion of the anchor through the stabilization band.

A portion of the anchor such as a bone screw may be driven through the first end of the stabilization band to create a hole through the stabilization band.

In other implementations, a portion of the anchor may engage the first end of the stabilization band. There are many possibilities but the concept is illustrated by examples such as a clamp mechanism that is tightened to reduce a space holding a portion of the stabilization band such that the stabilization band cannot move relative to the anchor. The first anchor may have an integral retainer or one that abuts the first anchor. Thus, in order to reduce the number of different components used for a facet joint stabilization assembly, a first anchor may be made from the same components as a second anchor and retainer, described in more detail below. The retainer may be applied to the end of the stabilization band and the stabilization band may pass through the first anchor before passing through a portion of the second anchor.

The combination of the second anchor and the retainer serves to allow the stabilization band to be moved relative to the second anchor and then to retain the moved stabilization band so that it cannot move relative to the second anchor to release the tension pulling the first anchor and the second anchor towards each other.

One implementation is to have an eyelet, channel, or an equivalent added to the second anchor so that a portion of the stabilization band may be pulled through the second anchor. One of skill in the art will recognize that a second anchor may use a channel that does not completely encircle a portion of the stabilization band as long as the channel allows the stabilization band to move through the channel and constrains the stabilization band from moving in a direction substantially perpendicular to the long axis of the stabilization band, the channel is sufficient. Thus, a second anchor may have a U-shaped component that is mechanically deformed after a stabilization band is moved into the open end of the U-shaped channel such that the channel constrains the stabilization band but may not totally encircle or surround a portion of the stabilization band.

The second anchoring means includes a cannulated split screw, and a snap lock pin with an eyelet plate with a portion of the facet stabilization band passing through an opening in the eyelet plate, the cannulated split screw adapted for placement into a bore hole in the vertebra before the snap lock pin with engaged eyelet plate is inserted into the cannulated split screw to expand portions of the cannulated split screw within the vertebra.

FIG. 8A is a side view of an illustration of an implementation with a first anchor 804 engaged with a stabilization band 808 through a pre-formed opening 812. A second anchor 816 is shown with a integral channel 820 through which the stabilization band may pass.

A retainer 824 may be slid down the second end of the stabilization band 828 until the retainer is abutting the second anchor 816. This movement of the retainer 824 to contact the second anchor 816 may be performed before the stabilization band 808 is moved relative to the second anchor (or before a tool is used to move the two anchors towards one another). Alternatively, the retainer 824 may be moved after the stabilization band 808 has been moved relative to the second anchor 816 in order to retain the new position of the stabilization band 808 relative to the second anchor 816.

FIG. 8B is a top view of the facet joint stabilization assembly in FIG. 8A. Note that after pulling on the second end of the stabilization band (See FIG. 8A) the first anchor 804 is now closer to the second anchor 816. In order to prevent the stabilization band from moving back through the channel 820 towards the first anchor, the retainer is used to hold the stabilization band. One of skill in the art will recognize that the use of many methods of retaining the position of the stabilization band relative to the second anchor may allow for some small movement of the stabilization band as the retainer engages with the stabilization band. There may be some movement of the retainer with respect to the second anchor that releases a small portion of the tension between the retainer and the first anchor. These minor movements and releases of tension do not alter the fact that retaining the position of the stabilization band after the stabilization band is moved relative to the second anchor maintains a substantial portion of the tensile force pulling the two anchors towards one another. One of skill in the art will recognize that surgeons will simply pull a bit more on the stabilization band to compensate for the minor relaxation inherent to that implementation.

The retainer may be a crimp that is mechanically deformed to alter the crimp from a channel that allows the stabilization band from passing through it, to a channel that does not allow the stabilization band to pass through it. The retainer may be some other type of anti-slip device.

Rather than a crimp that is a channel that encircles a portion of the stabilization band, the crimp may be a U-shaped channel that is slipped onto the stabilization band and mechanically deformed so that the stabilization band will not move relative to the deformed U-shaped channel under the expected loading.

Another implementation may use a retainer that has a channel with interdigitating teeth that are slanted to allow passage of the stabilization band in a first direction (away from the first anchor and second anchor) and resist movement of the stabilization band in the second direction (back towards the first and second anchor). Some surgeons may prefer implementations that allow the stabilization band to move in both directions relative to the retainer until the retainer is altered, other surgeons may prefer retainers that only allow motion of the stabilization band in one direction.

Other anti-slip mechanisms are known in the art and may be used in retainers that encircle or substantially surround a portion of the stabilization band. Cam-based devices may be used to allow motion in one direction as the stabilization band rotates the cam out of the way when moving in a first direction but causes the cam to engage the stabilization band and resist movement in the opposite direction.

The retainer may be integral to the second anchor rather than an independent component.

Instead of using an anti-slip device as a retainer, the stabilization band may be retained relative to the second anchor by tying a knot in the stabilization band so that is cannot pass through the second anchor. Likewise, the stabilization band may be tied to the second anchor to retain the relative position of the stabilization band.

In another implementation, the stabilization band may be retained relative to the second anchor by anchoring a portion of the stabilization band with a third anchor or by tying a portion of the stabilization band to a vertebral body.

Rather than using force applied to the stabilization band to pull the two anchors together to reposition the vertebrae, one could reposition the anchors using force applied directly to the anchors or the vertebrae then pull the stabilization band tight and retain the band in position to retain the position of the anchors.

Facet Joint Augmentation Assemblies.

Another therapy that may be applied to a facet joint is to augment the facet joint with a facet joint spacer to increase the distance between the inferior articular process and the superior articular process. This is know as distraction. Increasing the distance between the inferior articular process of one vertebra and the superior articular process of an adjacent more caudal vertebra will alter the relative positions of two vertebrae and may alter the loading on the disc that lies between the vertebral bodies of the two vertebrae. Increasing this distance may also separate two painful facet joint surfaces. Increasing the distance between the inferior articular process of one vertebra and the superior articular process of an adjacent more caudal vertebra may also enlarge a stenotic spinal canal and stenotic neuralforamina to relieve compressed nerves.

Insertion of a wedge shaped joint capsule spacer into the facet joint may allow for additional control upon the imposed relative movement of the inferior articular process relative to the superior articular process of the facet joint.

FIG. 9 is a perspective view of the distal end of an implementation of a facet joint dilator 900. In this context, distal/proximal are taken with respect to the hand of the surgeon. Thus, the portion of the device held by the surgeon would be on the proximal end and the end inserted into the body would be the distal end. The facet joint dilator has a foot 904 that may have a tapered leading edge 908. The facet joint dilator may have a concave face 912 and a convex face 916 to emulate the shape at point of entry of the facet joint. The angle between the foot 904 and the shaft 920 may be approximately perpendicular as shown in FIG. 9 but it may be some other angle including a simple extension of the shaft (a zero degree angle). The choice of angle between the foot and the shaft is driven by the access angle in order to access and dilate the facet joint. The access angle will vary depending on the particular motion segment at issue and the approach used by the surgeon. The dilator may be implemented with a flat face rather than a pair of convex and concave faces based on the geometry of the facet joint to be dilated. The dilator may be implemented so that the depth of the dilator beyond the tapered leading edge continues to increase along the foot towards the connection of the foot and the shaft. The dilator may be part of a set of dilators so that a series of dilators may be inserted in sequence to progressively increase the amount of imposed dilation of the facet joint. The dilator shaft may be in the range of between 4 millimeters and 12 millimeters and more often between 8 millimeters and 10 millimeters. When the foot is perpendicular to the shaft, the length of the foot may be between 5 millimeters and 15 millimeters.

Figure 5:
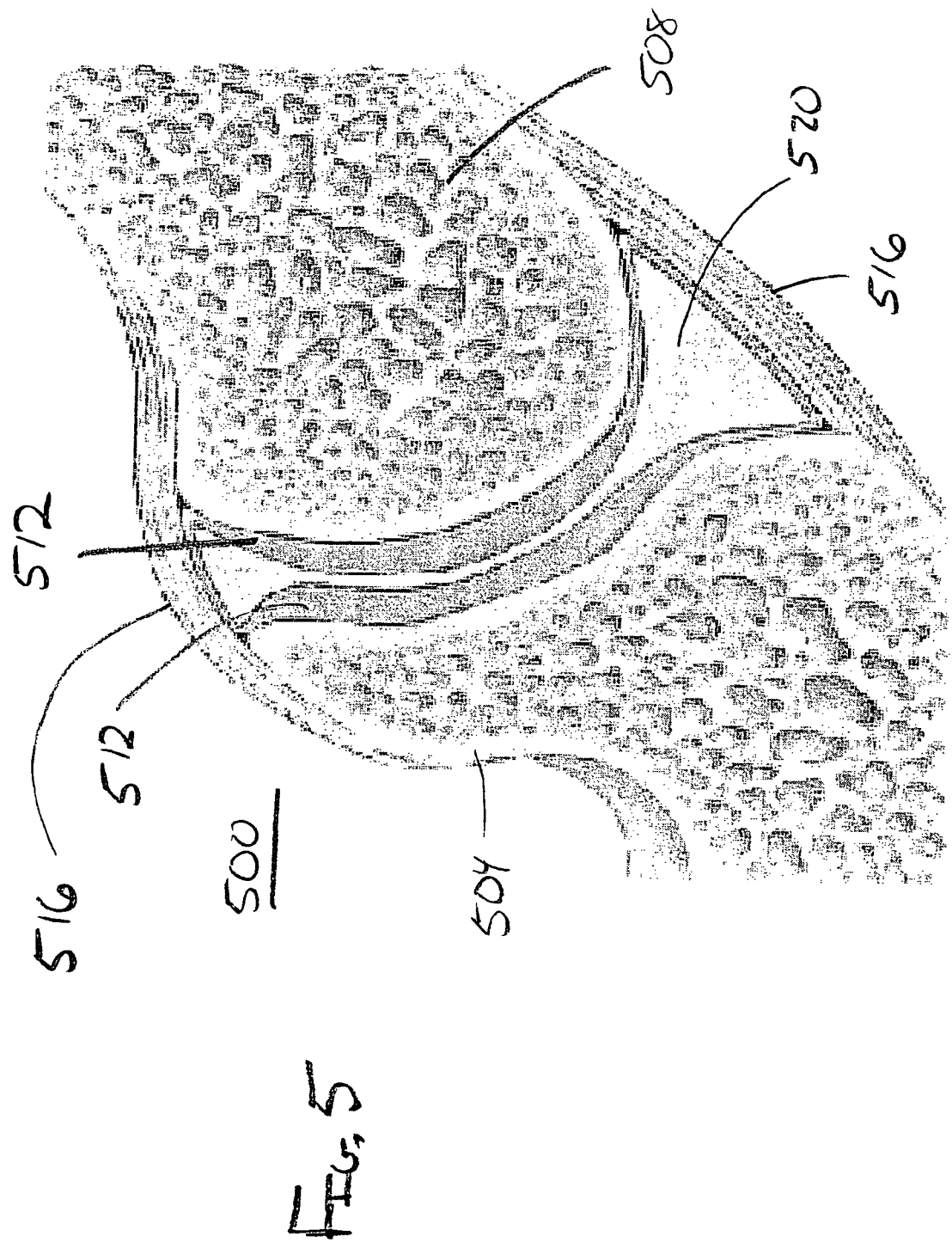
FIG. 5 is an enlarged cross section of a facet joint.

FIG. 10 is a caudal entry view of a facet joint without the joint capsule. (See element 516 in FIG. 5). The rear edge of the superior articular process 1004 is shown by a dashed line running through the inferior articular process 1008. Target line 1012 shows a place for the dilator. The facet joint capsule may be opened using a knife blade, an electrocautery process, a curette, an elevator, or other probe.

The insertion of a dilator through the facet joint capsule and into the facet joint to dilate the facet joint is facilitated if the dilator foot is lubricious (slippery). The dilator foot may be made of a lubricious material such as a polytetrafluoroethylene polymer including material sold under the Teflon trademark. Some implementations of the dilator foot may be treated with a surface coating to lubricate the surface.

After the dilation process creates a void to receive a facet joint spacer, a spacer may be inserted to retain and possibly increase the distraction between the inferior articular process and the superior articular process. The spacer may be shaped to include a wedge angle to distract part of the facet joint more than another part of the facet joint or to substantially mirror a physiological wedge angle that exists between the surfaces of the inferior articular process and the superior articular process.

Again, one of skill in the art will recognize that having the facet joint spacer made of or coated with a lubricious material will facilitate the process of inserting the facet joint spacer into the facet joint. The facet joint spacer may be made of a lubricious material such as a polytetrafluoroethylene polymer including material sold under the Teflon trademark. The facet joint spacer may be made of an ultrahigh molecular weight polyethylene (UHMWPE) or some other material (as described below). The facet joint spacer may be coated with a lubricant. The dimensions of the facet joint spacer may be in the range from between about 0.05 millimeters to about 6 millimeters in height often sized to achieve 0.05 millimeters to 4 millimeters of distraction; from between about 5 millimeters to about 15 millimeters in length, and often between about 8 millimeters to about 12 millimeters in length; from between about 5 millimeters to about 12 millimeters in width and often between about 8 millimeters to about 10 millimeters in width.

Figure 11:
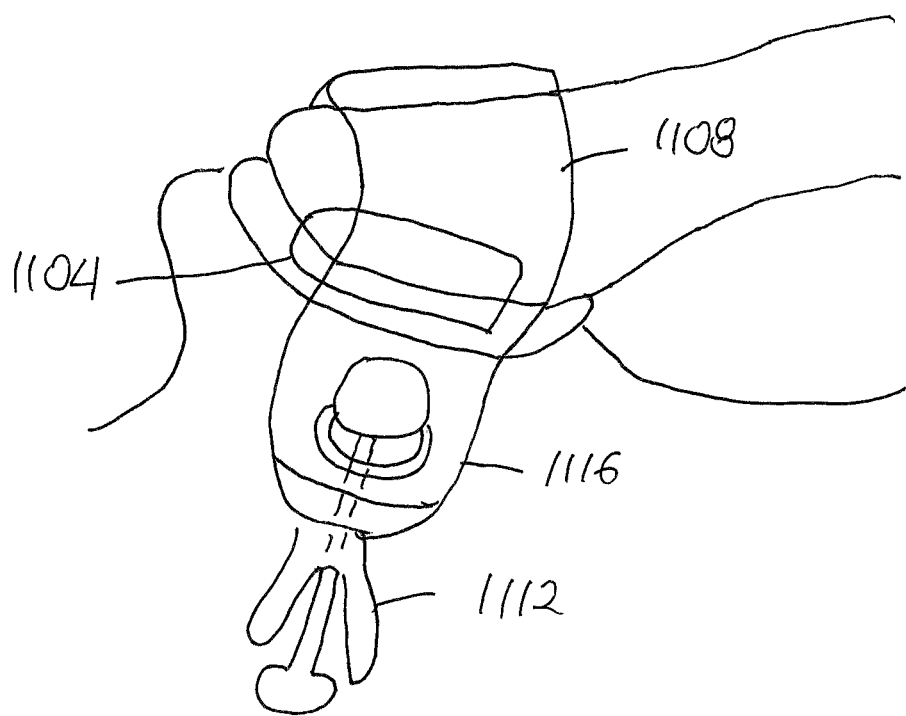
FIG. 11 is a caudal entry view of an implanted facet joint spacer 1104 retained by a facet joint stabilization assembly I 108 including a first anchor 1112 and a stabilization band 1116.

An inserted facet joint spacer may be held in place by a facet joint stabilization assembly as described above. FIG. 11 is a caudal entry view of an implanted facet joint spacer 1104 retained by a facet joint stabilization assembly 1108 including a first anchor 1112 and a stabilization band 1116.

Figure 12:
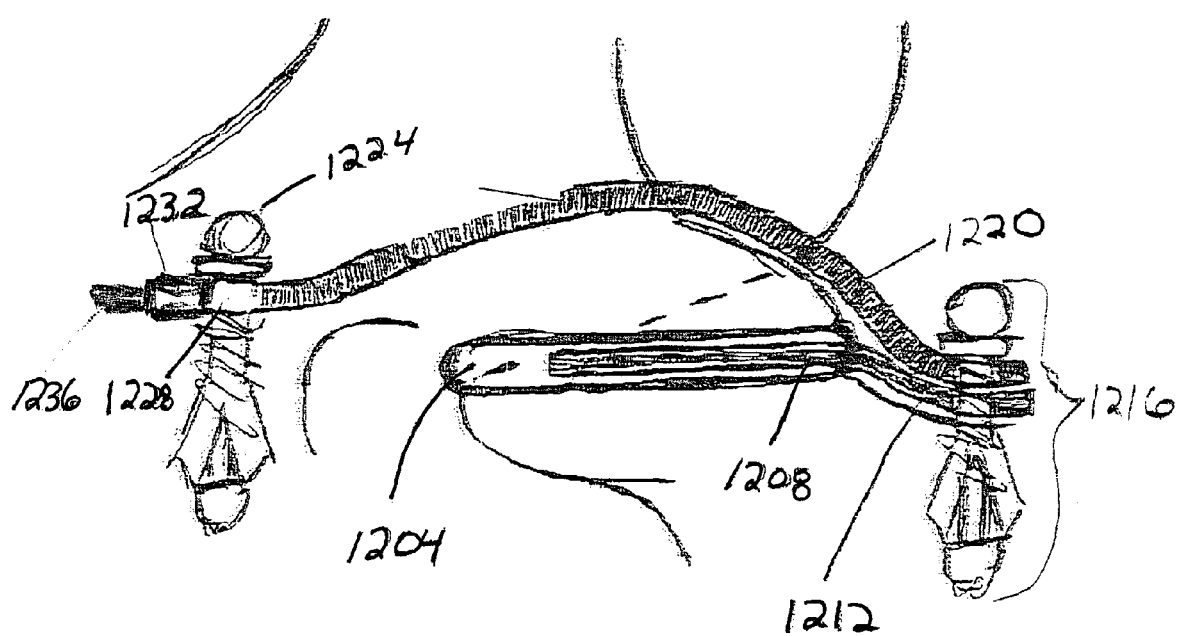
FIG. 12 is a view of an implementation of a facet joint augmentation assembly.

FIG. 12 is a view of an implementation of a facet joint augmentation assembly. In this implementation that facet joint 1204 is augmented with a facet joint spacer 1208 that has a tail section 1212 that extends out of the facet joint. The tail section may have a pre-formed hole that is engaged by the first anchor 1216 along with the pre-formed hole in the first end of the stabilization band 1220. (The tail section need not have a pre-formed hole as a hole may be added in situ, an anchor component may be driven through the tail section, or the tail section may be engaged with the first anchor in a manner not needing a component to pass through the tail section such as a clamp mechanism or one of the various anti-slip mechanism discussed elsewhere.) The stabilization band 1220 runs through a channel 1228 in the second anchor 1224 and is retained in a tensioned position by a mechanically deformed crimp 1232. The stabilization band 1220 may be cut close to the crimp to leave a new second end 1236 of the stabilization band.

Figure 13:
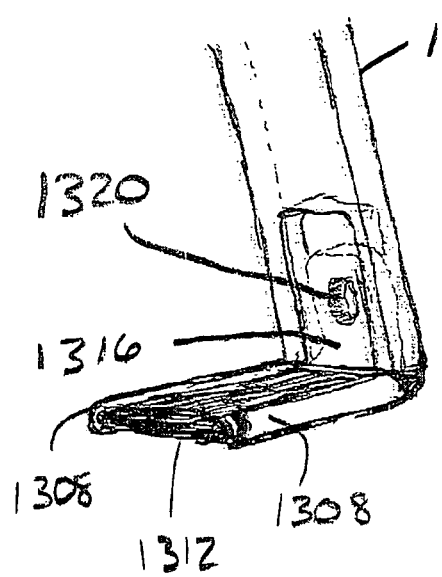
FIG. 13 is a view of an implementation of a facet joint spacer insertion tool 1304 with two arms 1308 with concave inner faces holding a facet joint spacer 1312 with a tail section 1316.

FIG. 13 illustrates an implementation of a facet joint spacer insertion tool 1304 with two arms 1308 with concave inner faces holding a facet joint spacer 1312 with a tail section 1316. The tail section 1316 has a pre-formed hole 1320.

Figure 14:
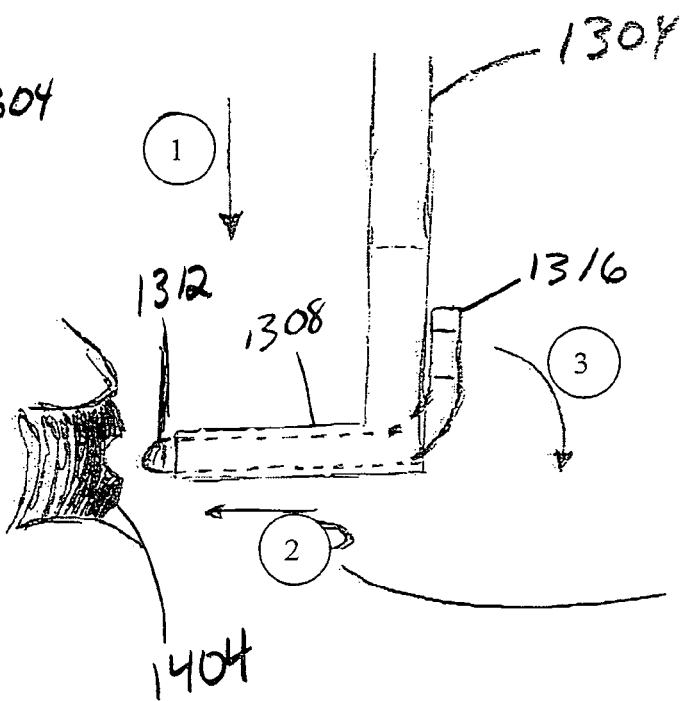
FIG. 14 is a side view of the same facet joint spacer insertion tool 1304 with a facet joint spacer 1312 shown with dashed lines behind arm 1308.

FIG. 14 is a side view of the same facet joint spacer insertion tool 1304 with a facet joint spacer 1312 shown with dashed lines behind arm 1308. The facet joint spacer 1312 may have a tapered leading edge and shown here with tail section 1316. The assembly process includes moving the loaded facet joint spacer insertion tool 1304 in proximity to the dilated facet joint 1404. The assembly process further includes inserting the loaded facet joint spacer insertion tool 1304 into the facet joint 1404 and then extending the tail section 1316.

Figure 15:
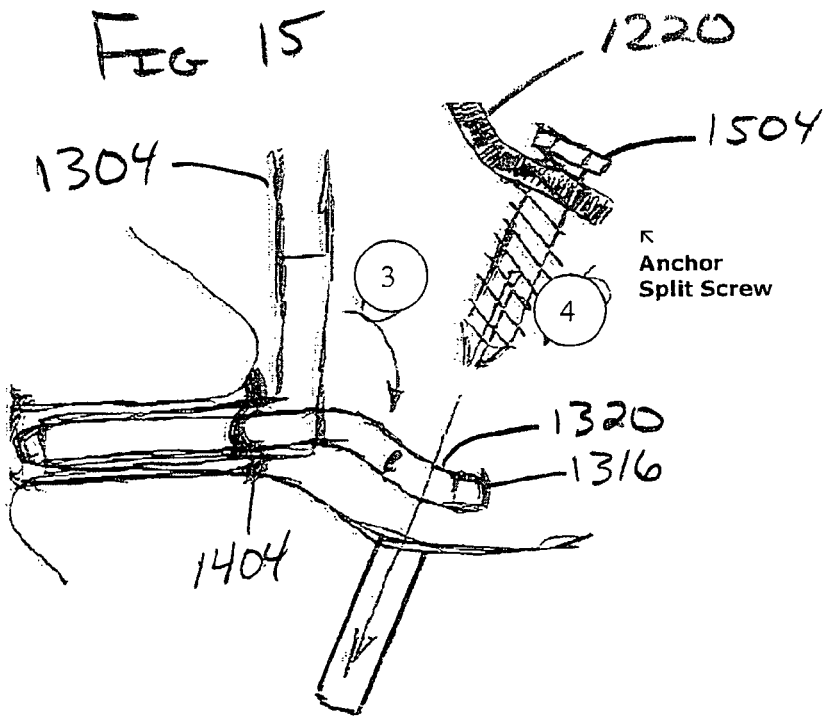
FIG. 15 illustrates the step of inserting a bottom portion 1504 of a first anchor through the pre-formed hole 1320 in the tail section 1316.

FIG. 15 illustrates the step of inserting a bottom portion 1504 of a first anchor through the pre-formed hole 1320 in the tail section 1316. The bottom portion 1504 of the first anchor may be inserted into a previously formed bore in the vertebra. The bottom portion 1504 of the first anchor is shown here as engaged with the first end of the stabilization band 1220 as the bottom portion 1504 passes through a pre-formed hole in the stabilization band. The bottom portion 1504 of the first anchor is shown here as a threaded cannulated fastener with threaded fingers at the implanted end of the bottom portion 1504 of the first anchor.

Figure 16:
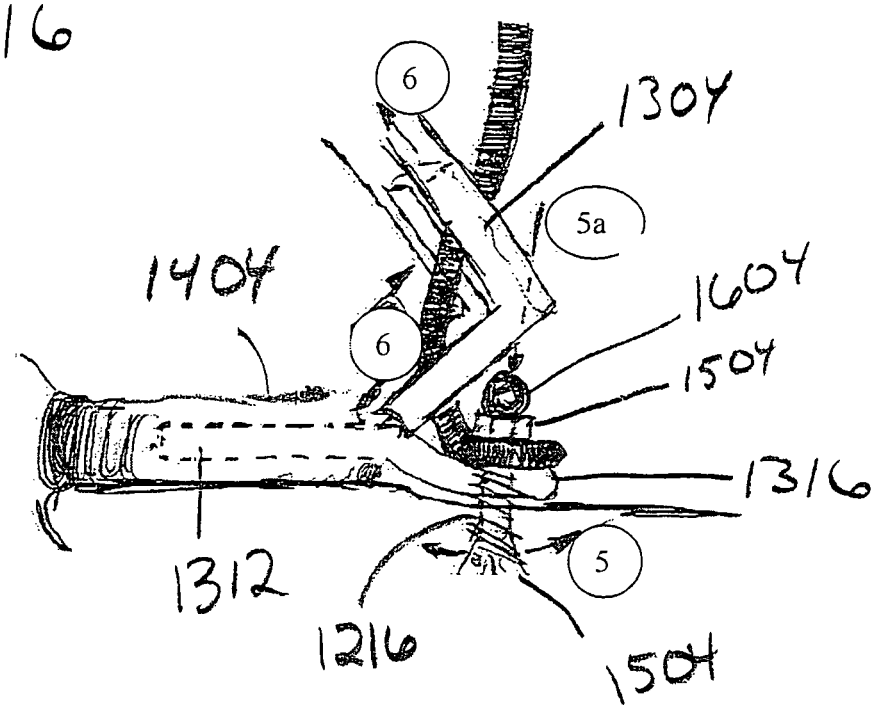
FIG. 16 illustrates additional steps subsequent to those shown in FIG. 15 for one implementation.

FIG. 16 illustrates the steps in this implementation of inserting the second portion 1604 of the first anchor to splay the fingers at the inserted end of the bottom portion 1504 of the first anchor. Once the tail portion 1316 of the facet joint spacer 1312 is anchored in place by the completed first anchor 1216, the facet joint spacer delivery device 1304 may be removed from the facet joint 1404.

Figure 17:
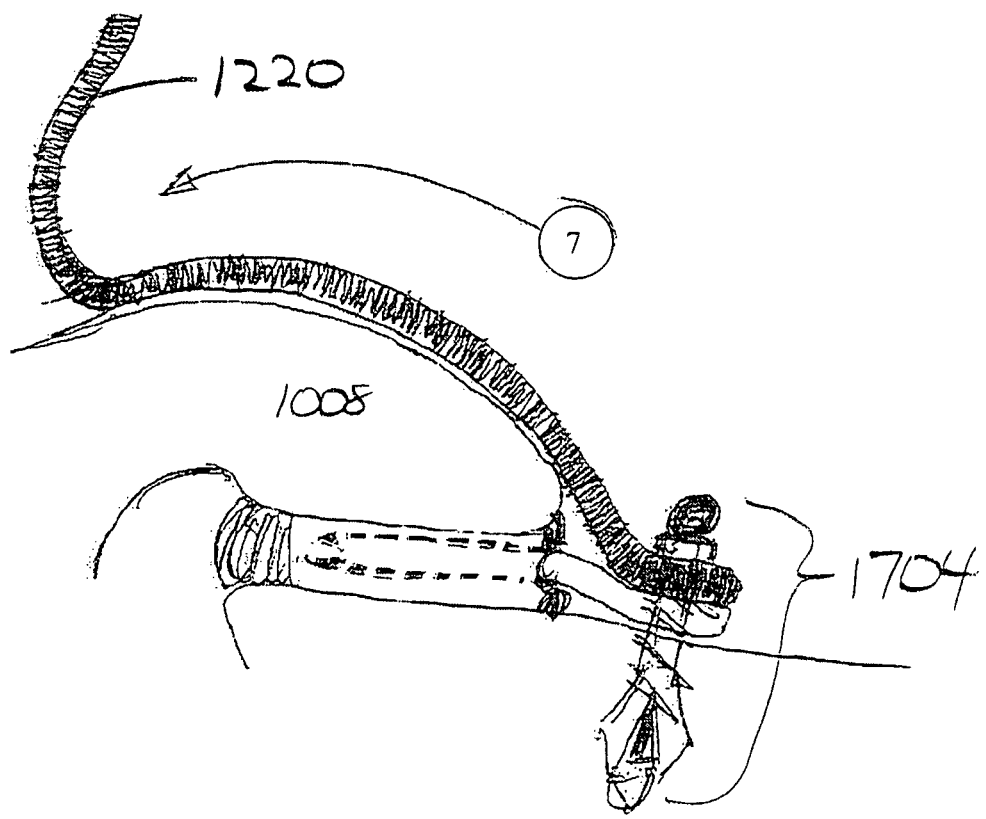
FIG. 17 illustrates the step in this implementation of moving the free end of the stabilization band 1220 away from the first anchor 1704 and over the inferior articular process 1008 towards the site for the placement of the second anchor.

FIG. 17 illustrates the step in this implementation of moving the free end of the stabilization band 1220 away from the first anchor 1704 and over the inferior articular process 1008 towards the site for the placement of the second anchor.

Figure 18:
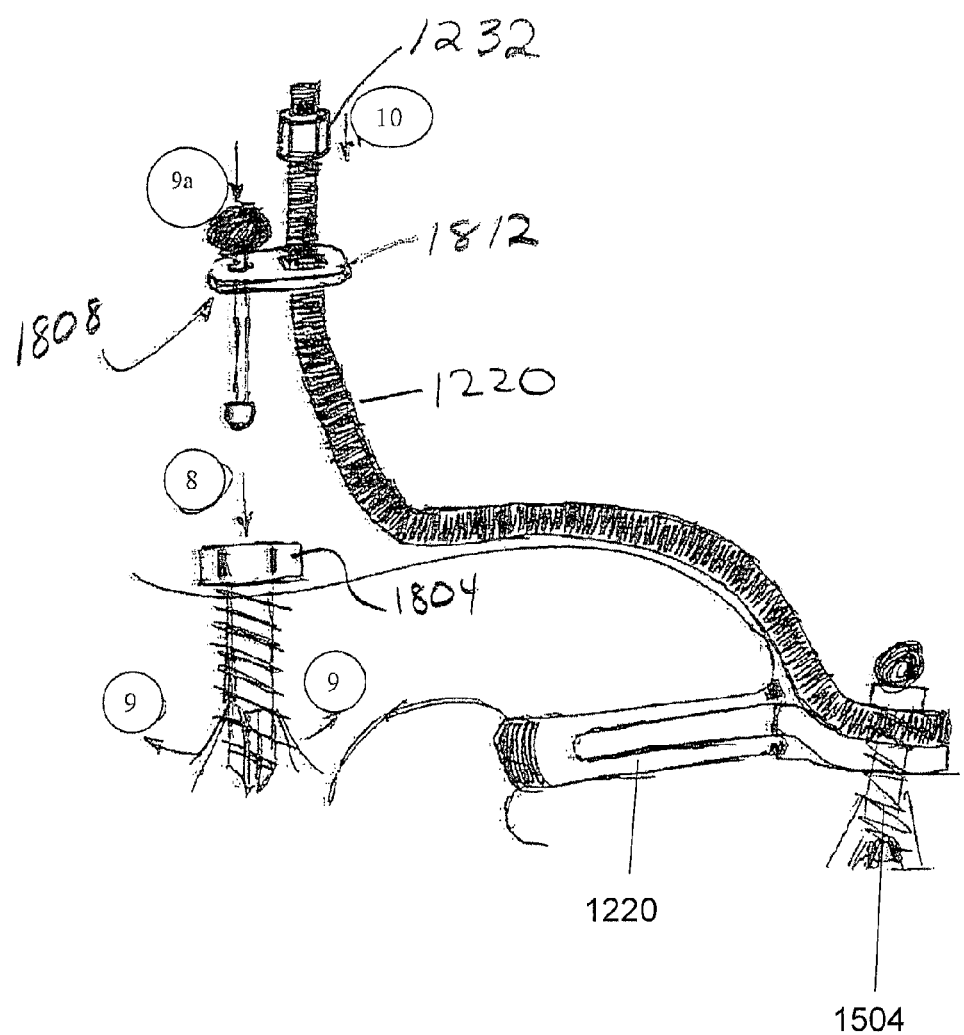
FIG. 18 illustrates the steps in this implementation of placing the bottom portion 1804 of the second anchor into the vertebra.

FIG. 18 illustrates the steps in this implementation of placing the bottom portion 1804 of the second anchor into the vertebra. The implementation may insert the bottom portion 1804 in a pre-formed bore hole. The bottom portion 1804 of the second anchor may be the same as the bottom portion 1504 of the first anchor. An expander pin 1808 passes through one side of a connector plate 1812 and the loose end of the stabilization band 1220 passes through the other side of the connector plate 1812. Insertion of the expander pin 1808 into the bottom portion 1804 of the second anchor will splay the fingers at the inserted end of the bottom portion 1504 of the second anchor. Crimp 1232 may be slid down the stabilization band 1220 until the crimp 1232 abuts the second anchor.

Figure 19:
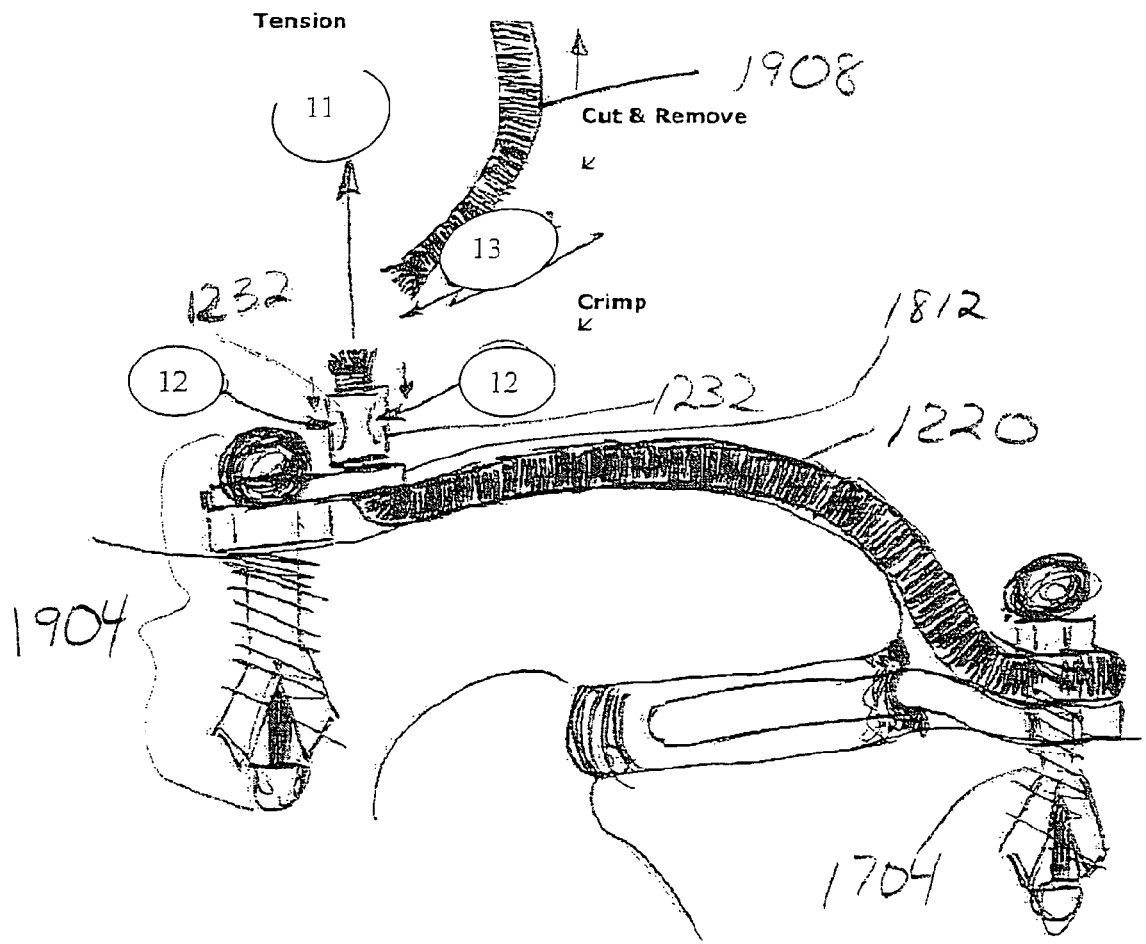
FIG. 19 illustrates the steps of this implementation to pull on the stabilization band 1220 to move a portion of the stabilization band through the connector plate 1812 that is connected to the second anchor 1904.

FIG. 19 illustrates the steps of this implementation to pull on the stabilization band 1220 to move a portion of the stabilization band through the connector plate 1812 that is connected to the second anchor 1904. As the stabilization band is pulled through the connector plate 1812, tension is applied that pulls the second anchor 1904 towards the first anchor and the tension pulls the first anchor towards the second anchor. After the application of the desired amount of tension, the crimp 1232 may be mechanically deformed to retain the stabilization band 1220 to maintain the tensile force between the first anchor and the crimp 1232 that abuts the connection plate 1812 of the second anchor 1904. The excess portion 1908 of the stabilization band 1220 may be cut and removed.

Rigid Fixation of Facet Joint.

Figure 20B:
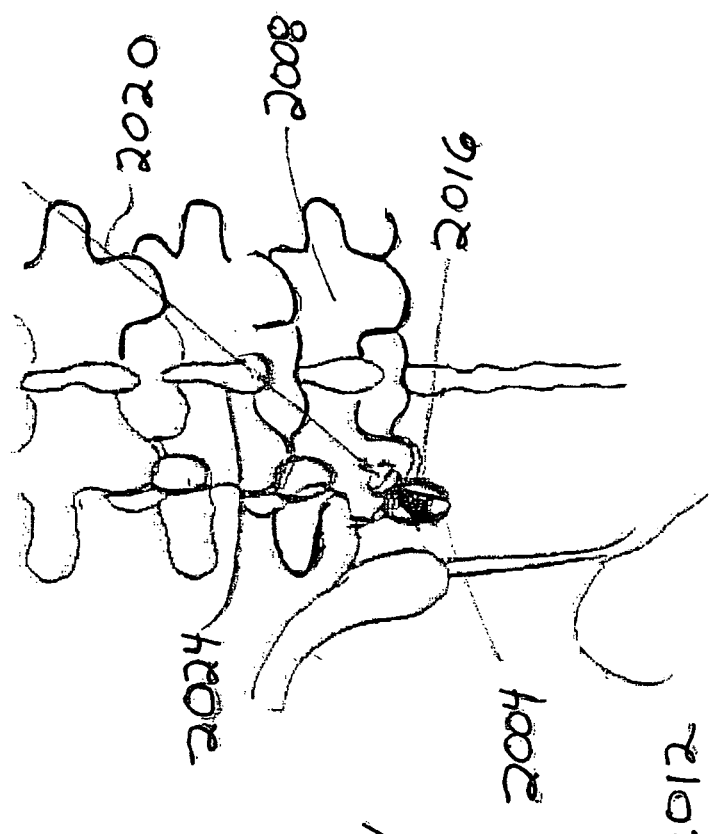
FIG. 20B shows the same spine from a posterior view.
Figure 20A:
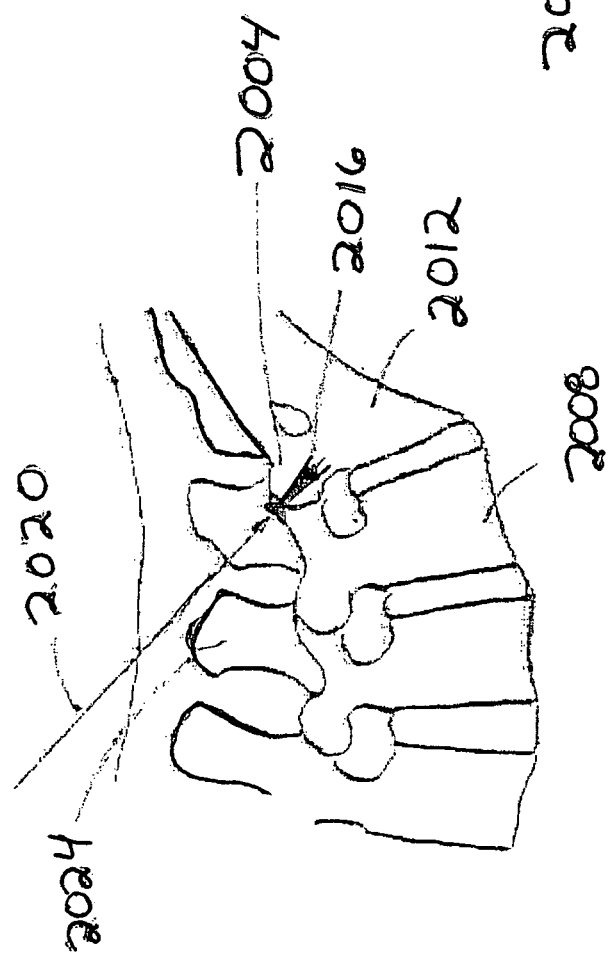
FIG. 20A is a lateral view of a spine of a patient receiving rigid fixation of the left side L5-S1 facet joint 2004 (shown without the facet joint capsule).

FIG. 20A is a lateral view of a spine of a patient receiving rigid fixation of the left side L5-S1 facet joint 2004 (shown without the facet joint capsule). FIG. 20B shows the same spine from a posterior view. Surgical procedures on the posterior of the spine are frequently performed on a patient lying prone on the operating table. The rigid fixation may be applied bilaterally by applying fixation to the right side L5-S1 facet joint (not shown). The L5-S1 facet joint lies between an inferior articular process of the L5 vertebra 2008 and an articular process of the sacrum 2012 (See FIG. 4) that effectively, acts as the superior articular process. The fixation device 2016 may be inserted along the line of approach 2020 that comes close to the caudal edge of the L4 spinous process 2024. The fixation device may be inserted through a previously placed stabilization band from a facet joint stabilization assembly (not shown in FIG. 20). The fixation device may be inserted through a previously placed facet joint insert. The fixation device may be placed in an appropriately sized and previously formed bore that may be made by drilling or other processes known in the art. The fixation device may include a first component that has external threads to engage the vertebra and is capable of being expanded when a second component is inserted into a cavity in the long axis of the first component. The expansion may be the splaying of fingers of the first component as the second component is inserted into the embedded first component. The expansion may be achieved by the deformation of an embedded first component in response to rotation of a second component that engages female threads in the first component to distort the first component in a manner analogous to a molly bolt fastener. An anchor of the type shown in FIGS. 7A and 7B may be employed. Other implementations may use a second component that serves as an expander tip that is threaded so that the upper portion 6f the expander tip engages with corresponding female threads in the interior of the first component.

Figure 21:
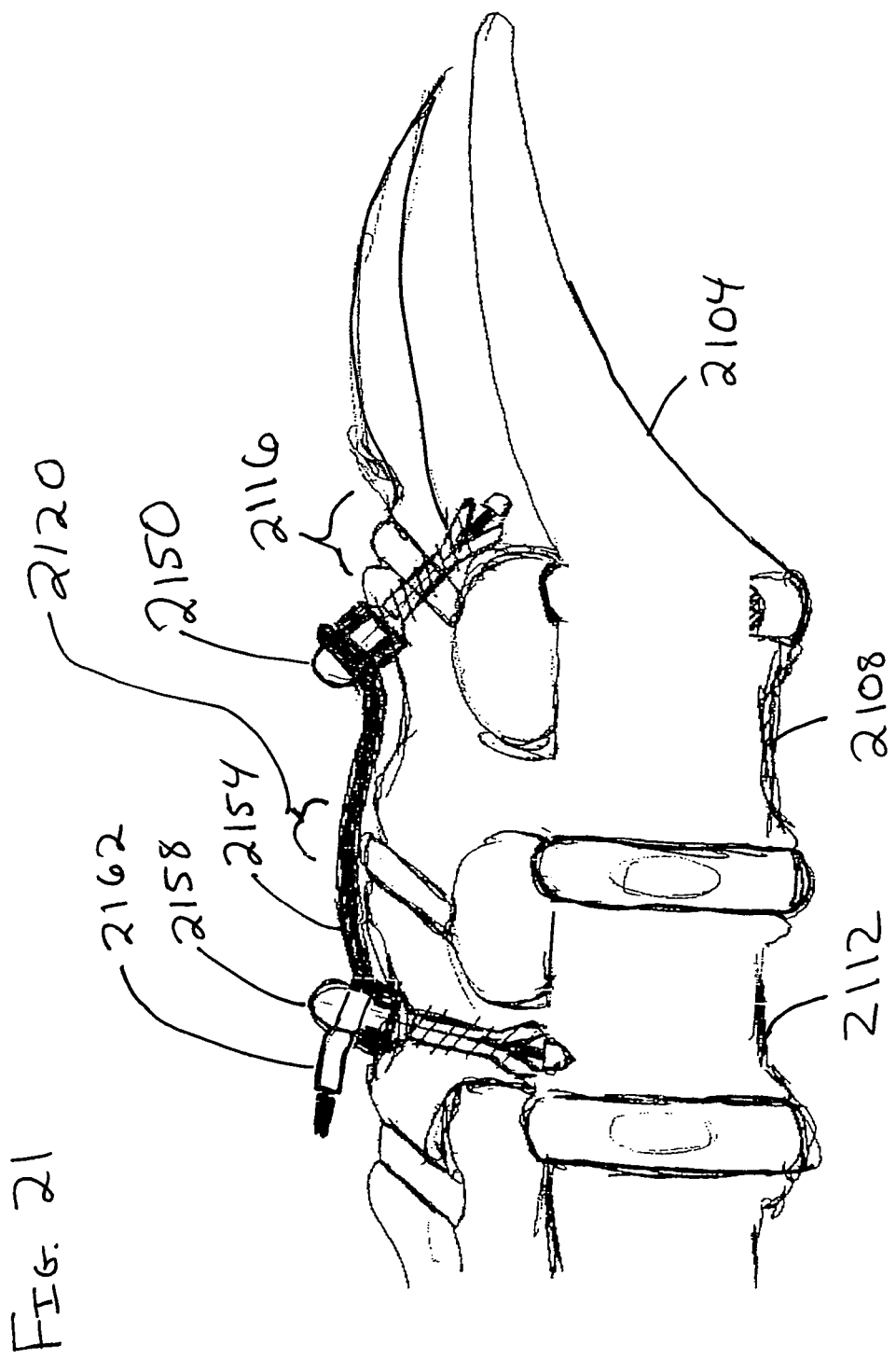
FIG. 21 is a side view of a spine of a patient in prone position after receipt of a facet joint stabilization assembly.

FIG. 21 is a side view of a spine of a patient in prone position after receipt of a facet joint stabilization assembly. The sacrum 2104, L5 vertebra 2108, and L4 vertebra 2112 are of interest in this Figure. The first anchor 2150 is inserted across the L5/S I facet joint 2116 visible in this view. In this implementation, the stabilization band 2154 runs through a portion of the second anchor 2158 and a retainer 2162. Thus, first anchor 2150 serves to immobilize the facet joint 2116 and assist in the therapy applied to facet joint 2120 on the left side of the L4/L5 motion segment.

Additional Comments on Materials.

There implementations may include certain materials that may enhance visualization of implant assembly components and instrumentation for their deployment via radio-imaging (e.g., fluoroscopy). It will be understood that such enhancing materials (e.g., Ta; barium sulfate powders, etc.) may be incorporated into the formation of certain metal or polymeric materials in the device assemblies and may be incorporated into tools sets used to deploy the various components.

The various components may be made from biocompatible materials where, the term "biocompatible" refers to an absence of chronic inflammation response or cytotoxicity when or if physiological tissues are in contact with, or exposed to (e.g., wear debris) the materials and devices. The materials used may be selected to be one or more of the following: sterilizable; visible; imageable, e.g., fluoroscopically; or via CT (computed tomography), or MRI (magnetic resonance imaging), with this last-named imaging technique mandating that materials be substantially free of Fe (iron). Moreover, in consideration of contrast, detail, and spatial sensitivity, materials may use contrast media (e.g., iodine) or other materials (e.g., Ta; Ti, barium sulfate) when and where needed and appropriate, to supplement or modify radiolucency or radio-opaqueness.

Materials may be configured to include biocompatible materials that meet ISO 10993 standards for long-term implants, are able to withstand, without wear, long term normal ranges of physiological loading (i.e., over the lifetime of the implant, or up to about $40 \times 10^6$ cycles) of between about 1250 Newtons (N) (280 lbf) and 2250 N (500 lbf) axial compression; 100 N (25 lbf) and 450 N (100 lbf) of both lateral and sagittal shear, respectively, through full ROM. Additionally, certain components may be designed to tolerate short term (e.g., over about 20 continuous cycles) maximum physiological loads through full range of motion of about 8000 Newtons (N) (1800 lbf) axial compression; about 2000 N (450 lbf) lateral shear; and about 3000 N (675 lbf) sagittal shear, without failing.

The biomechanical properties of components used in the various therapies described above may be designed to substantially match those of native structures, to functionally enable the assemblies to substantially mimic physiologic load distribution and dissipation; prevent ongoing transition syndrome degeneration while exhibiting sufficient resistance to fatigue and shear forces to preclude device wear and material fragmentation. The facet joint spacers and snap lock pins may be fabricated from medical grade cross-linked UHMWPE; medical grade polyether-ether-ketone (PEEK) such as that commercially available from Invibio Inc., in Lancashire, United Kingdom, or polyether-ketone-ketone (PEKK) available from Coors-Tech Corporation, in Colorado, or alternatively, conventional polymethylmethacrylate (PMMA); or other suitable polymers.

Anchor components such as cannulated screws may be formed from among high strength (high tensile strength, high fatigue strength), wear and abrasion resistant metal alloys (for example: MP35N; Elgiloy,™ a super alloy of cobalt chrome; Co—Cr alloy such as Stellite™; Ti6Al4V alloy, and nitride coated Ti alloys).

Access and Deployment.

While the assemblies, tools, and methods described above are not limited to a specific method of access to the posterior of a motion segment, those less familiar with the state of the art may benefit from an overview of one sequence of steps that may be used to access the site. The following steps may be used to provide access for deployment.

Access to a posterior target site on the spine such as the posterior of the L5-S1 segment and deployment of the assemblies described above may be performed following percutaneous entry, as the components and tools are deployed to the motion segment using introducer tubes, guide wires, dilators, and exchange system instrumentation as known in the art. More specifically, the components and tools may be introduced after a blunt-tipped stylet is introduced percutaneously through a guide pin introducer under fluoroscopic guidance and safely enables advancement of the guide pin introducer through the soft tissue of the posterior access track up to the target site on a spinal vertebral body. The stylet is withdrawn from the guide pin introducer now positioned in place at the target site, and a beveled guide pin, often of about 0.09 inch to about 0.125 inch of outer diameter is inserted, with its handle attached by engagement means of a hex and thumb screw lock, into the guide pin introducer, forming a guide pin-guide pin introducer assembly. While still utilizing fluoroscopic guidance to appropriately maintain alignment, the beveled tip at the distal end of the guide pin is advanced through the dorsal fascia of the spinous process at the target site of the vertebral body. The guide pin is advanced through the intervening soft tissue to the L5-S1 facet joints (left side first). The thumb screw is loosened and the guide pin handle is removed from the guide pin's proximal end, to enable attachment of the guide pin extension. The guide pin introducer is then removed without disturbing the guide pin.

Next, a cannulated dilator (e.g., about 6 millimeter in diameter) is inserted over the guide pin extension and its distal end is advanced over the guide wire to the vertebral body target site. The process is sequentially repeated inserting larger a cannulated dilator, and then the dilator is swept to expose the target L5-S1 bone surface.

The dilator is part of an assembly in engagement with a tapered dilator sheath, respectively inserted over the guide pin and advanced to the target facet joint site. A series of dilators of up to 20 millimeter in diameter are often used. Thus, dilators in 4 millimeter increments from 6 millimeters up to 20 millimeters in diameter. The dilator handle is then disengaged from the sheath and the dilator is withdrawn over the guide pin, leaving the dilator sheath in place, to preserve trajectory. The guide pin is then removed to enable insertion of a 2 millimeter drill for subsequent deployment of facet anchors through the dilator sheath. The drill is used to drill (through the large dilator sheath down to bony surface) into the L5-S1 facet joint cortical bone to accommodate, anchors such as titanium alloy facet screws of between about 2 millimeters to about 6 millimeters in length and often about 2 millimeters in diameter.

Then, following removal of the drill, the guide pin, is inserted through the dilator sheath, and the exchange bushing is inserted over the pin, over the dilator sheath and advanced to the target site. Then, the exchange cannula is inserted over the exchange bushing, and left in place following subsequent removal of the bushing. The dilator is then inserted into the dilator sheath, to engage and remove it.

At this point in the procedure, components such as the facet joint spacers; cannulated anchors and snap lock pin assemblies are introduced over the guide wire and through the exchange system, i.e., by deploying the distal end of the left anchor component by means of insertion over the proximal end of the extended guide pin and into the pre-drilled hole. Next, the 2-piece, first anchor is put into place, the second anchor is put into place; the stabilization band is tensioned and retained using a crimp tube then cut.

Additional Variations.

It will be understood that the surgical access may be conducted by methods other than the posterior approach referenced-above, including open surgical procedures from any access orientation, and that each of the therapies to the spine discussed above may be conducted on more than one motion segments traversed by at least one working channel, with deployment of appropriate implants and with post-procedural surgical closure. It will be further understood that the length and dimensions of implant components (e.g., anchors, snap lock pins; stabilization bands, facet joint spacers, facet joint dilators, facet joint spacer tools) described above will depend in part on the nature of the treatment procedure and the physical characteristics of the patient, as well as the construction materials and intended functionality, as will be apparent to those of skill in the art.

Many implementations seeking dynamic stabilization of a facet joint will employ a stabilization band that will elongate under stress. As the stabilization band increases resistance to stretching with flexion of the spine, the stabilization band tends to hamper the flexion of the motion segment which may be a desired outcome as this may protect an impaired disc from damage.

Some implementations may seek to severely limit the movement of the facet joint and may employ a substantially inelastic stabilization band that does not increase length appreciably in response to load. This may be used with or without an anchor driving through the facet joint to stabilize the joint.

Kits may be provided that include all of the components necessary for deploying one of the therapies described above. The kits may also include some or all of the necessary dilators and insertion tools. The kits may include components and tools in a variety of sizes and configurations to address the variations in facet joints from one portion of a spine to another, from one patient to another, and to address irregularities that may be present from degeneration of the facet joint.

While various implementations of the invention have been described, it will become apparent to those of ordinary skill in the art that many more implementations are possible within the scope of this invention. Accordingly, the invention is not to be restricted except in light of the attached claims and their equivalents.

What is claimed is:

1. A facet joint augmentation assembly comprising:

a facet joint spacer including an insertion segment configured for insertion into a facet joint between a superior articular process of a vertebra and an adjacent inferior articular process of a vertebra, the facet joint spacer comprising a facet joint spacer tail configured to extend out of the facet joint, the facet joint spacer tail having a pre-formed opening;

a facet stabilization band with a first end and a second end, the first end having an opening;

a first screw that is cannulated;

a second screw that is cannulated;

wherein the second screw extends through an aperture in a connector plate that is smaller in diameter than a head of the second screw;

wherein the facet stabilization band extends through the connector plate with a mechanical crimp secured at the second end of the facet stabilization band; and wherein the first screw extends through the opening of the first end of the facet stabilization band and the pre-formed opening of the facet joint spacer tail.

2. The facet joint augmentation assembly of claim 1, wherein the first screw is split at an end thereof and has a first expander pin having a shaft with a first enlarged region at a first end and a second enlarged region at a second end opposite the first end, wherein largest diameters of the first enlarged region and the second enlarged region are greater than a largest diameter of a shaft portion extending between the first and second ends; and wherein the second screw is and split at an end and has a second expander pin having a shaft with a first enlarged region at a first end and a second enlarged region at a second end opposite the first end, wherein largest diameters of the first enlarged region and the second enlarged region are greater than a largest diameter of a shaft portion extending between the first and second ends.

3. The facet joint augmentation assembly of claim 1 wherein the facet joint spacer is comprised of a lubricious material that facilitates inserting the facet joint spacer into the facet joint.

4. The facet joint augmentation assembly of claim 3 wherein the facet joint spacer is comprised of a polytetrafluoroethylene polymer that facilitates inserting the facet joint spacer into the facet joint.

* * * * *